United States Patent
Wang et al.

(10) Patent No.: US 8,367,720 B2
(45) Date of Patent: Feb. 5, 2013

(54) ANDROGRAPHOLIDE DERIVATIVES AND USE THEREOF IN MANUFACTURE OF MEDICAMENTS

(75) Inventors: Yuqiang Wang, Guangzhou (CN); Xiaojian Jiang, Guangzhou (CN); Jie Jiang, Guangzhou (CN); Zaijun Zhang, Guangzhou (CN); Zhaoqi Yang, Guangzhou (CN); Pei Yu, Guangzhou (CN)

(73) Assignee: Panorama Research Inc., Sunnyvale, CA (US)

( * ) Notice: Subject to any disclaimer, the term of this patent is extended or adjusted under 35 U.S.C. 154(b) by 384 days.

(21) Appl. No.: 12/672,476

(22) PCT Filed: Aug. 7, 2008

(86) PCT No.: PCT/CN2008/071919
§ 371 (c)(1),
(2), (4) Date: Feb. 5, 2010

(87) PCT Pub. No.: WO2009/018780
PCT Pub. Date: Feb. 12, 2009

(65) Prior Publication Data
US 2011/0077295 A1    Mar. 31, 2011

(30) Foreign Application Priority Data
Aug. 8, 2007    (CN) .......................... 2007 1 0029644

(51) Int. Cl.
| | | |
|---|---|---|
| A01N 43/08 | (2006.01) | |
| A01N 57/00 | (2006.01) | |
| A61K 31/34 | (2006.01) | |
| A61K 31/665 | (2006.01) | |
| A61K 31/585 | (2006.01) | |
| C07D 307/02 | (2006.01) | |
| C07D 307/00 | (2006.01) | |

(52) U.S. Cl. ........ 514/473; 514/100; 514/175; 549/477; 549/313

(58) Field of Classification Search .................. 514/473, 514/100, 175; 549/477, 313
See application file for complete search history.

(56) References Cited

FOREIGN PATENT DOCUMENTS

| CN | 1433757 A | 8/2003 |
|---|---|---|
| CN | 1478774 A | 3/2004 |
| CN | 101125850 A | 2/2008 |
| JP | 63088124 A | 4/1998 |
| WO | 01/57026 A1 | 8/2001 |
| WO | 2006/101538 A2 | 9/2006 |

*Primary Examiner* — Samira Jean-Louis
(74) *Attorney, Agent, or Firm* — Maschoff Gilmore & Israelsen

(57) ABSTRACT

The present invention relates to an andrographolide derivative of the formula (I), wherein $R_1$, $R_2$ and $R_3$ are same or different substituents selected from hydrogen, substituted or unsubstituted organic acid radicals, inorganic acid radicals, alkyl, aryl or heteroaryl, and at least one of $R_1$, $R_2$ and $R_3$ is R-lipoic acid, S-lipoic acid or a mixture thereof, or corresponding dihydrolipoic acids thereof, or N-acetylcysteine radical. The derivative has good antitumor effect, can induce apoptosis of tumor cells, can directly kill Gram-positive bacteria (*staphylococcus aureus*) and drug resistance bacteria (MRSA5676 and MRSA5677), can inhibit the QS-system of Gram-negative bacteria (*Pseudomonas aeruginosa*), can inhibit and destroy the formation of biofilm of *Pseudomonas aeruginosa*; and exhibits significant hypoglycemic effect, so that it can be used in manufacture of medicaments for treatment of cancers, inflammation, diabetes, and bacterial and viral infections.

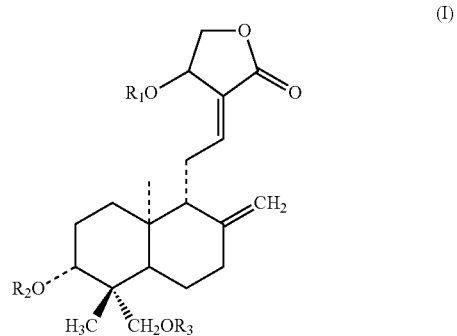

(I)

11 Claims, 5 Drawing Sheets

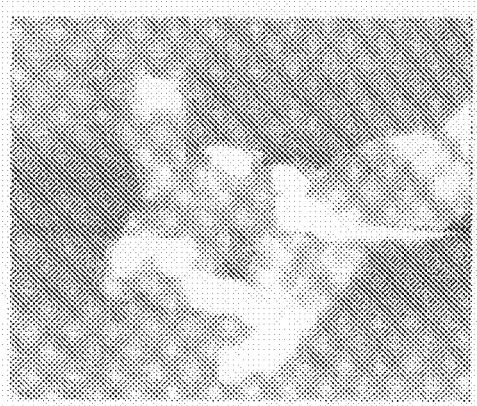
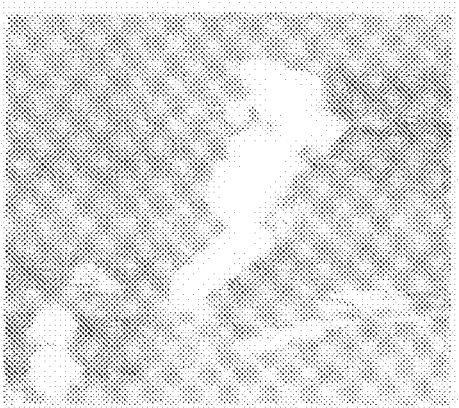
Fig.5-1
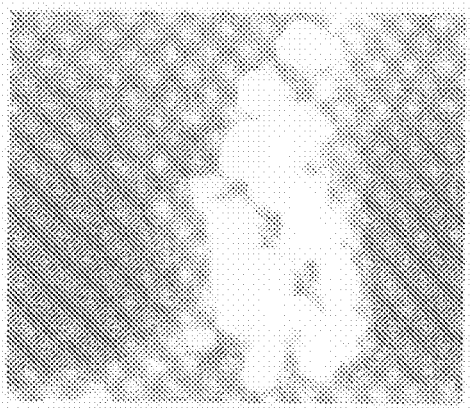
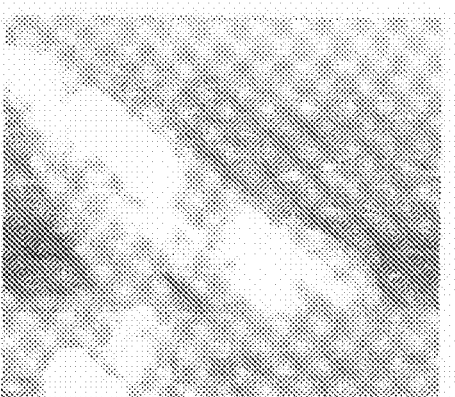
Fig.5-2
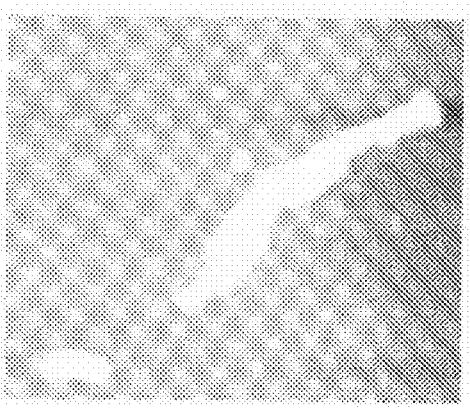
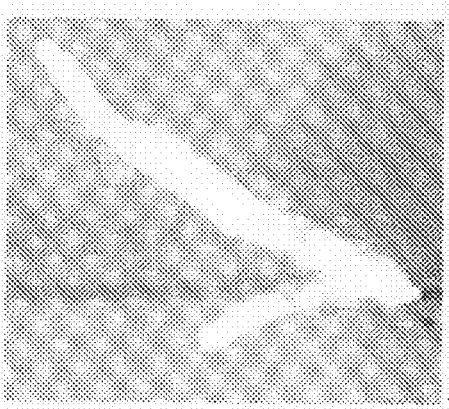
Fig.5-3

ANDROGRAPHOLIDE DERIVATIVES AND USE THEREOF IN MANUFACTURE OF MEDICAMENTS

FIELD OF INVENTION

The present invention relates to novel andrographolide derivatives and use thereof in manufacture of medicaments.

BACKGROUND OF THE INVENTION

Andrographolide (Andro) is the main active component of the herb Andrographis (Chinese name: "Chuanxinlian" or "穿心莲"; Latin name: *Herba Andrographitis Paniculatae*). Andrographis Herb is widely used in many Asia countries including China, India, Japan, Korea, etc. for the treatment of inflammatory diseases including rheumatic arthritis, pharyngolaryngitis, diarrhea, and bacterial and viral infections (Zhao and Fang, Chin. Med. J. (Engl) 1991, 104, 770-775; Puri et al., J. Nat. Prod. 1993, 56, 995-999; Zhang and Tan, Clin. Exp. Pharmacol. Physiol. 1996, 23, 675-678; Zhang and Tan, Clin. Exp. Pharmacol. Physiol. 2000, 27, 358-363; Shen et al., Br. J. Pharmacol. 2002, 35, 399-406). A recent report indicated that andrographolide inhibited a broad-spectrum of cancers and exhibited good therapeutic effects (Rajagopal et al., J. Exp. Ther. Oncol. 2003, 3, 147-158; Satyanarayana et al. Science 2003, 299, 363-370). In Malaysia, Andrographis is widely used for the treatment of diabetes. During the last 30 years, andrographolide and its 3 derivatives, potassium dehydroandrograpolide succinate ("Chuanhuning" or "穿琥宁"), potassium sodium dehydroandrographolide succinate ("Yanhuning" or "炎琥宁") and andrographolide sodium bisulfite ("Lianbizhi" or "莲比治") have been widely used in the clinic in China. The structure formulas of andrographolide (Andro) and its derivatives, Chuanhuning, Yanhuning and Lianbizhi are as follows:

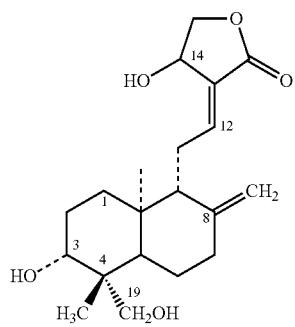

Andro

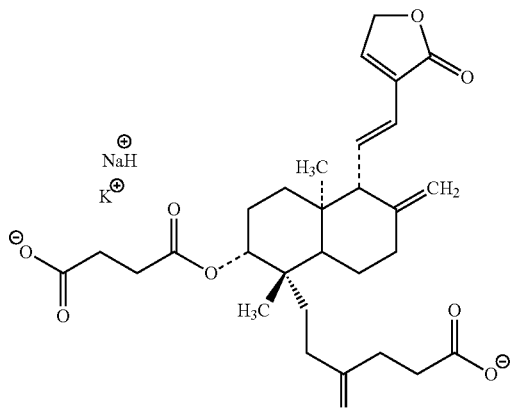

Chuanhuning

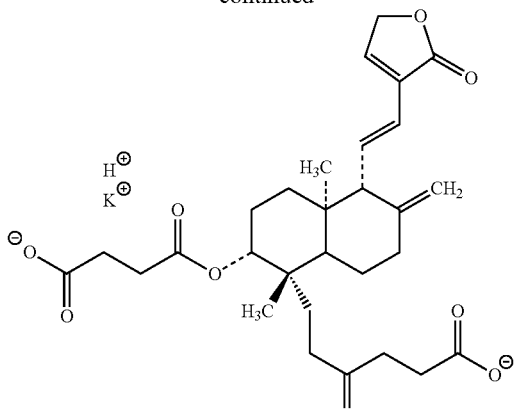

Yanhuning

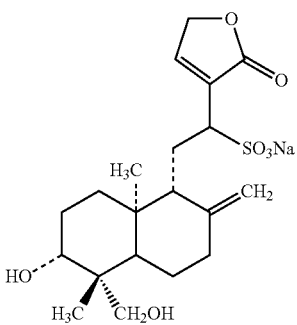

Lianbizhi

These drugs can alleviate clinical symptoms of inflammation, fever, and bacterial and viral infection diseases (Hendrickson et al., J. Bacteriol. 2001, 183, 7126-7134; Zhang and Tan, Clin. Exp. Pharmacol. Physiol. 1996, 23, 675-678; Zhang et al., Clin. Exp. Pharmacol. Physiol. 2000, 2358-368; Shen et al., Br. J. Pharmacol. 2002, 35, 399-406; Gabrielian et al., Phytomedicine 2002, 9, 589-597).

SUMMARY OF THE INVENTION

One embodiment provides andrographolide derivatives.

Another embodiment provides a pharmaceutically acceptable salt of the andrographolide derivatives.

Another embodiment provides a process for preparing the andrographolide derivative, a pharmaceutically acceptable salt thereof, and a pharmaceutical composition thereof.

Another embodiment provides a use of an andrographolide derivative in manufacture of a medicament for treatment of diseases such as bacterial and viral infections, inflammation, cancers, and diabetes mellitus. Another embodiment provides a method for the treatment of diseases such as bacterial and viral infections, inflammations, cancers, and diabetes mellitus, comprising administrating a patient in need of the treatment a therapeutically effective amount of an andrographolide derivative.

The andrographolide derivative of the present invention has a structure of the formula I:

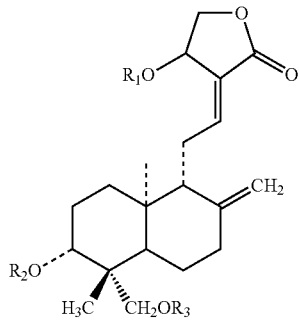

Wherein $R_1$, $R_2$ and $R_3$ can be the same or different, and each independently represent hydrogen, or a substituted or unsubstituted group selected from: organic acid radicals, such as fatty acid radicals and aromatic acid radicals, including acetic acid radical, propionic acid radical, butanoic acid radical, malonic acid radical, pyruvic acid radical, cinnamic acid radical, succinic acid radical, citric acid radical, lactic acid radical, gluconic acid radical, 5-[1,2]dithiolan-3-yl-pentanoic acid radical (lipoic acid radical), N-acetylcysteine radical, amino acid radical, benzoic acid radical and inorganic acid radicals, such as sulfuric acid radical, nitric acid radical, phosphoric acid radical, and salts thereof; alkyl, aryl, heteroaryl and the like, with the proviso that at least one of $R_1$, $R_2$ and $R_3$ is lipoic acid ("lipoic acid" always refers to R-lipoic acid or S-lipoic acid or racemic lipoic acid and its corresponding dihydrolipoic acids) or N-acetylcysteine.

According to the novel andrographolide derivative of the formula I, the compound of the present invention is of a structure of the formula II:

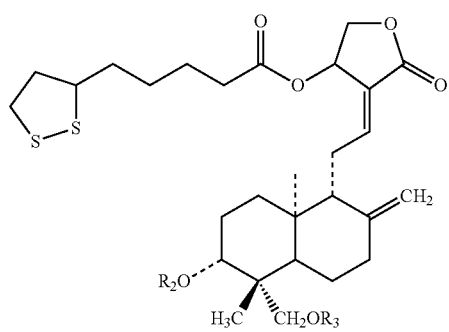

Wherein $R_2$ and $R_3$ can be the same or different, and each independently represent hydrogen, or a substituted or unsubstituted group selected from: organic acid radicals, such as fatty acid radicals and aromatic acid radicals, including acetic acid radical, propionic acid radical, butanoic acid radical, malonic acid radical, pyruvic acid radical, cinnamic acid radical, succinic acid radical, citric acid radical, lactic acid radical, gluconic acid radical, lipoic acid radical, N-acetylcysteine, amino acid radical, benzoic acid radical and inorganic acid radicals, such as sulfuric acid radical, nitric acid radical, phosphoric acid radical, and salts thereof; alkyl, aryl, heteroaryl and the like.

According to the novel andrographolide derivative of the formula I, the compound of the present invention is of a structure of the formula III:

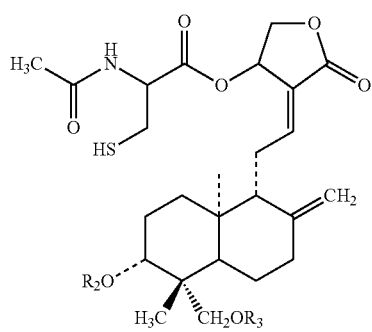

Wherein $R_2$ and $R_3$ can be the same or different, and each independently represent hydrogen, or a substituted or unsubstituted group selected from: organic acid radicals, such as fatty acid radicals and aromatic acid radicals, including acetic acid radical, propionic acid radical, butanoic acid radical, malonic acid radical, pyruvic acid radical, cinnamic acid radical, succinic acid radical, citric acid radical, lactic acid radical, gluconic acid radical, lipoic acid radical, N-acetylcysteine, amino acid radical, benzoic acid radical and inorganic acid radicals, such as sulfuric acid radical, nitric acid radical, phosphoric acid radical, and salts thereof; alkyl, aryl, heteroaryl and the like.

According to the novel andrographolide derivative of the formula II, the preferred compound of the present invention is the compound of formula AL-1:

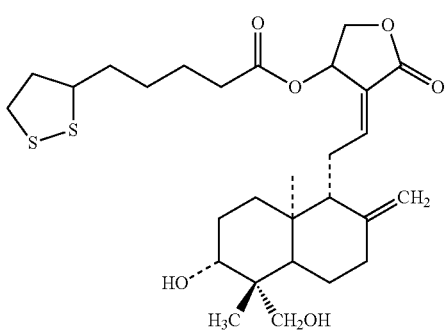

According to the novel andrographolide derivative of the formula III, the preferred compound of the present invention is the compound of the formula A-AC:

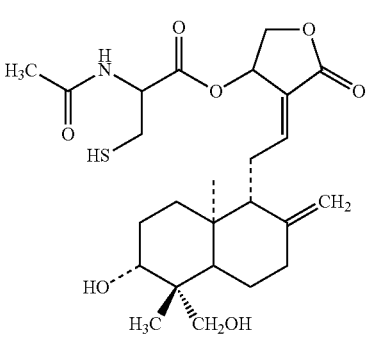

The present invention further provides the compounds of formulas AG, AF, ACl and ANO:

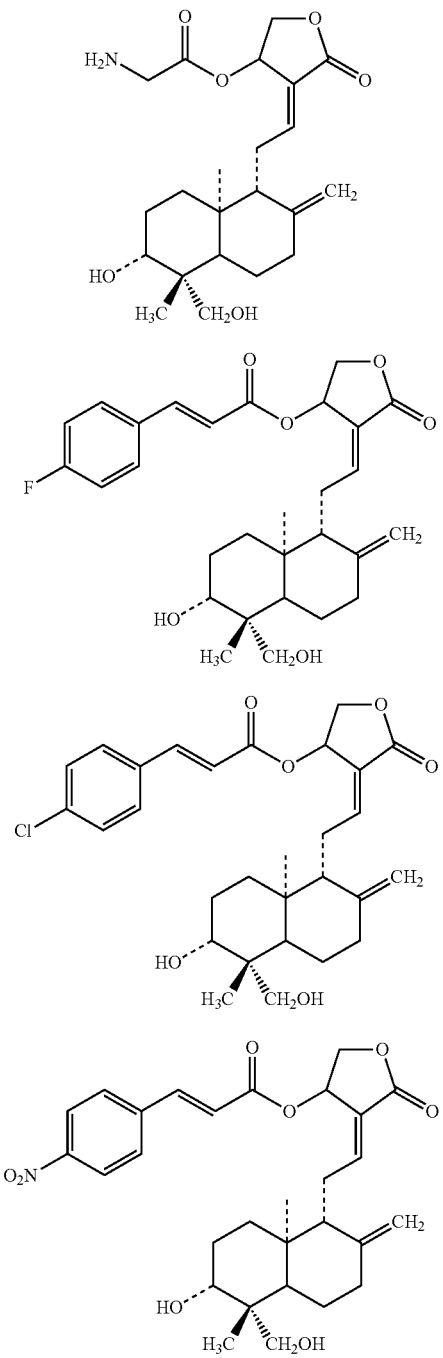

The present invention also relates to a pharmaceutical composition comprising a compound of the formula I or a compound of the formula AG, AF, ACl or ANO, and to a use of the pharmaceutical composition for the treatment of diseases including bacterial and viral infections, inflammations, cancers and diabetes mellitus. The pharmaceutical composition comprises a pharmaceutically effective amount of a compound of formula I or a compound of formula AG, AF, ACl or ANO, or a pharmaceutically acceptable salt thereof.

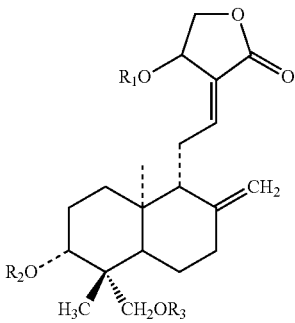

Wherein $R_1$, $R_2$ and $R_3$ can be the same or different, and each independently represent hydrogen, or a substituted or unsubstituted group selected from: organic acid radicals, such as fatty acid radicals and aromatic acid radicals, including acetic acid radical, propionic acid radical, butanoic acid radical, malonic acid radical, pyruvic acid radical, cinnamic acid radical, succinic acid radical, citric acid radical, lipoic acid radical, N-acetylcysteine, amino acid radical, benzoic acid radical and inorganic acid radicals, such as sulfuric acid radical, nitric acid radical, phosphoric acid radical and salts thereof; alkyl, aryl, heteroaryl and the like, with proviso that at least one of $R_1$, $R_2$ and $R_3$ is lipoic acid (always refers to R-lipoic acid or S-lipoic acid or racemic lipoic acid and its corresponding dihydrolipoic acids thereof) or N-acetylcysteine.

The present invention also relates to a pharmaceutical composition comprising a compound of the formula II, and to a use of the pharmaceutical composition for the treatment of diseases including bacterial and viral infections, inflammations, cancers and diabetes mellitus. The pharmaceutical composition comprises a pharmaceutically effective amount of a compound of formula II or a pharmaceutically acceptable salt thereof.

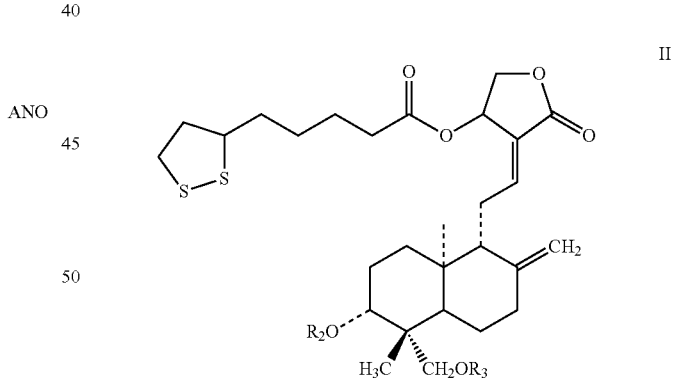

Wherein $R_2$ and $R_3$ can be the same or different, and each independently represent hydrogen, or a substituted or unsubstituted group selected from: organic acid radicals, such as fatty acid radicals and aromatic acid radicals, including acetic acid radical, propionic acid radical, butanoic acid radical, malonic acid radical, pyruvic acid radical, cinnamic acid radical, succinic acid radical, citric acid radical, lactic acid radical, gluconic acid radical, lipoic acid radical, N-acetylcysteine, amino acid radical, benzoic acid radical and inorganic acid radicals, such as sulfuric acid radical, nitric acid radical, phosphoric acid radical and salts thereof; alkyl, aryl, heteroaryl and so on.

The present invention also relates to a pharmaceutical composition comprising a compound of the formula III, and to a use of the pharmaceutical composition for the treatment of diseases including bacterial and viral infections, inflammations, cancers and diabetes mellitus. The pharmaceutical composition of the present invention comprises a pharmaceutically effective amount of a compound of formula III or a pharmaceutically acceptable salt thereof.

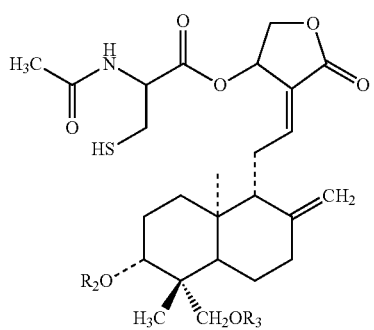

III

Wherein $R_2$ and $R_3$ can be the same or different, and each independently represent hydrogen, or substituted or unsubstituted substituents selected from: organic acid radicals, such as fatty acid radicals and aromatic acid radicals, including acetic acid radical, propionic acid radical, butanoic acid radical, malonic acid radical, pyruvic acid radical, cinnamic acid radical, succinic acid radical, citric acid radical, lactic acid radical, gluconic acid radical, lipoic acid radical, N-acetylcysteine, amino acid radical, benzoic acid radical and inorganic acid radicals, such as sulfuric acid radical, nitric acid radical, phosphoric acid radical and salts thereof; alkyl, aryl, heteroaryl and the like.

The present invention also relates to a pharmaceutical composition comprising the compound AG or ANO, and to a use of the pharmaceutical composition for the treatment of diseases including bacterial and viral infections, inflammations, cancers and diabetes mellitus. The pharmaceutical composition comprises a pharmaceutically effective amount of the compound AG or ANO or a pharmaceutically acceptable salt thereof.

Andrographolide can inhibit NF-κB, while NF-κB plays an important role in the occurrence, development, angiogenesis and metastasis of tumors, and tumor microenvironment induced NF-κB expression, and many cancers involve high expression of NF-κB, thereby inducing the drug resistance of cancers. Andrographolide is also used for treatment of bacterial and viral infections, inflammations and diabetes mellitus, etc. Alpha-lipoic acid is an effective antioxidant and exhibits therapeutical effects on many diseases, such as bacterial and viral infections, inflammations, diabetes mellitus and complications thereof. The compound of the present invention can be in the form of a conjugate of andrographolide and an antioxidant such as alpha-lipoic acid, and has multiple mechanisms of action and therapeutic effects for many diseases. Thus, the andrographolide derivative of the present invention is different from and superior to andrographolide derivatives existing in the prior art.

The novel andrographolide derivative of the present invention is used as an anticancer agent for treatment of cancers or drug-resistant cancers, or as an antimicrobial agent for treatment of bacterial and viral infections, or as an antidiabetic agent. Due to the unique structural features of the compounds of the present invention, they have many therapeutic effects including but not being limited to antibacterial, antiviral, antiinflammatory, antitumor and antidiabetic effects.

BRIEF DESCRIPTION OF THE DRAWINGS

FIG. 2 is a diagram showing inhibition of andrographolide derivatives according to the present invention on the growth of *Pseudomonas aeruginosa*; in which Andro, and AL-1 respectively have a concentration of 1 mM; while Chuanhuning, Yanhuning and Lianbizhi respectively have a concentration of 10 mM;

FIG. 3 is a diagram showing inhibition of andrographolide derivatives according to the present invention on the secretion of pyocyanine, in which Andro, and AL-1 respectively have a concentration of 1 mM; while Chuanhuning, Yanhuning and Lianbizhi respectively have a concentration of 10 mM;

FIG. 4 is a diagram showing inhibition of andrographolide derivatives according to the present invention on the activity of extracellular protease, in which Andro, and AL-1 respectively have a concentration of 1 mM; while Chuanhuning, Yanhuning and Lianbizhi respectively have a concentration of 10 mM;

FIG. 5-1, FIG. 5-2 and FIG. 5-3 are electron microscopic pictures showing the growth morphology of *Pseudomonas aeruginosa* in drug-free control group, Andro group and AL-1 group, where Andro and AL-1 respectively have a concentration of 1 mM;

FIG. 6-1, FIG. 6-2, FIG. 6-3 and FIG. 6-4 are electron microscopic pictures showing the early BF formation of *Pseudomonas aeruginosa* in drug-free control group, Andro group, Chuanhuning group and AL-1 group, where Andro and AL-1 respectively have a concentration of 1 mM, and Chuanhuning has a concentration of 10 mM; and FIG. 7-1, FIG. 7-2, FIG. 7-3 and FIG. 7-4 are electron microscopic pictures showing the mature BF formation of *Pseudomonas aeruginosa* in drug-free control group, Andro group, Chuanhuning group and AL-1 group, where Andro and AL-1 respectively have a concentration of 1 mM, and Chuanhuning has a concentration of 10 mM.

DESCRIPTION OF THE PREFERRED EMBODIMENTS

1. Definitions

Figures 1, 2, 3:
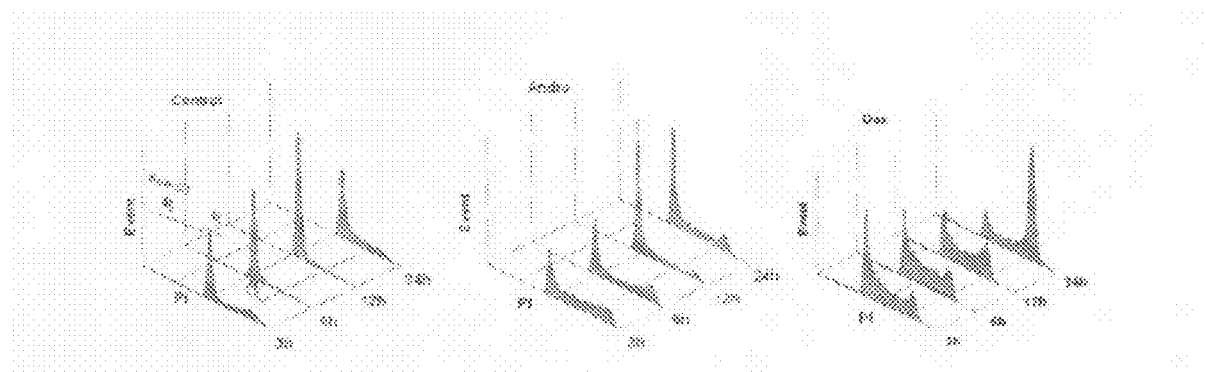
FIG. 1-1 to FIG. 1-8 are diagrams showing the effects of andrographolide derivatives according to the present invention on cell cycle and induction of apoptosis.

The term "organic acid" used in the present invention refers to saturated and unsaturated fatty acids and aromatic acids, in which fatty acids include but are not limited to alkyl-containing fatty acids, alkenyl-containing fatty acids, and alkynyl-containing fatty acids.

The term "alkyl" used in the present invention refers to unsubstituted or substituted straight, branched or cyclic alkyl chain having up to 15 carbon atoms. The straight alkyl includes, for example, methyl, ethyl, n-propyl, n-butyl, n-pentyl, n-hexyl, n-heptyl and n-octyl. The cyclic alkyl ("cycloalkyl") includes, for example, cyclopropyl, cyclobutyl, cyclopentyl and cyclohexyl. Alkyl can be substituted with one or more substituents. The non-limiting examples of the substituents include $NH_2$, $NO_2$, $N(CH_3)_2$, $ONO_2$, F, Cl, Br, I, OH, $OCH_3$, $CO_2H$, $CO_2CH_3$, CN, aryl and hetroaryl. The term "alkyl" also refers to unsubstituted or substituted straight, branched or cyclic alkyl having up to 15 carbon atoms and at least one heteroatom (e.g., nitrogen, oxygen or sulfur) in its chain. The above straight alkyl includes, for example, $CH_2CH_2OCH_3$, $CH_2CH_2N(CH_3)_2$ and $CH_2CH_2SCH_3$. The branched alkyl includes, for example, $CH_2CH(OCH_3)CH_3$, $CH_2CH(N(CH_3)_2)CH_3$ and $CH_2CH(OCH_3)CH_3$. The cyclic alkyl includes, for example, $CH(CH_2CH_2)_2O$, $H(CH_2CH_2)_2NCH_3$ and $CH(CH_2CH_2)_2S$. The above alkyl can be substituted by one or more substituents. The non-limiting examples of the substituents include $NH_2$, $NO_2$, $N(CH_3)_2$, $ONO_2$, F, Cl, Br, I, OH, $OCH_3$, $CO_2H$, $CO_2CH_3$, CN, aryl and heteroaryl.

The term "aryl" used in the present invention refers to unsubstituted or substituted aromatic compounds, carbocycle groups and heteroaryls. Aryl is either a monocyclic compound or a fused polycyclic compound. For example, phenyl is a monocyclic aryl, and naphtyl is a fused polycyclic aryl. Aryl can be substituted with one or more substituents. The non-limiting examples of the substituents include $NH_2$, $NO_2$, $N(CH_3)_2$, $ONO_2$, F, Cl, Br, I, OH, $OCH_3$, $CO_2H$, $CO_2CH_3$, CN, aryl and heteroaryl.

Heteroaryl relates to substituted or unsubstituted monocyclic or polycyclic groups, in which its ring comprises at least one heteroatom, such as nitrogen, oxygen and sulfur. For example, a typical heteroaryl comprising one or more nitrogen atoms is exemplified as tetrazolyl, pyrrolyl, pyridyl (such as pyrid-4-yl, pyrid-3-yl, pyrid-2-yl), pyridazinyl, indyl, quinolyl (such as quinol-2-yl, quinol-3-yl), imidazolyl, isoquinolyl, pyrazolyl, pyrazinyl, pyrimidinyl, pyridonyl or pyridazinyl; a typical hetroaryl comprising one oxygen atom includes fur-2-yl, fur-3-yl or benzofuryl; a typical hetroaryl comprising one surfur atom includes thienyl, benzothienyl; a typical heteroaryl comprising more than one kind of heteroatoms includes furoazetidinyl, oxazolyl, isoxazolyl, thiazolyl and phenothioxinyl. The heteroaryl can be substituted with one or more substituents including $NH_2$, $NO_2$, O-alkyl, NH-alkyl, $N(alkyl)_2$, NHC(O)-alkyl, $ONO_2$, F, Cl, Br, I, OH, $OCF_3$, $OSO_2CH_3$, $CO_2H$, $CO_2$-alkyl, CN, aryl and polyaryl. Also encompassed are heteroaryls with a heteroatom in the ring being oxidized, for example, N-oxide, ketone or sulfone.

The term "pharmaceutically acceptable" means that a compound has no unacceptable toxicity in a salt or excipient. Pharmaceutically acceptable salts comprise inorganic anions, such as chlorine ion, bromine ion, iodine ion, sulfuric acid radical, sulfurous acid radical, nitric acid radical, nitrous acid radical, phosphoric acid radical, etc. Organic anions include acetic acid radical, pyruvic acid radical, propionic acid radical, cinnamic acid radical, tosylic acid radical, citric acid radical, lactic acid radical, gluconic acid radical, etc. Pharmaceutically acceptable excipients are described below (see also, E. W. Martin, in Remington's Pharmaceutical Sciences Mack Publishing Company (1995), Philadelphia, Pa., 19th ed).

The term "amino acid" used in the present invention refers to natural and synthetic amino acids, wherein 24 natural amino acids include: alanine, arginine, asparagine, aspartic acid, citrulline, cysteine, cystine, glutamine, glutamic acid, glycine, histidine, hydroxyproline, leucine, isoleucine, lysine, methionine, ornithine, phenylalanine, proline, serine, threonine, tryptophane, tyrosine, valine, and synthetic amino acids include: 2-fluorophenylalanine, 3-fluorophenylalanine, 4-fluorophenylalanine, 2-chlorophenylalanine, 3-chlorophenylalanine, 4-chlorophenylalanine, 2,4-dichlorophenylalanine, 3,4-dichlorophenylalanine, 2-bromophenylalanine, 4-bromophenylalanine, 4-iodophenylalanine, 4-nitrophenylalanine, 2-methylphenylalanine, 3-methylphenylalanine, 4-methylphenylalanine, 2-cyanophenylalanine, 3-cyanophenylalanine, 4-cyanophenylalanine, homophenylalanine, allylglycine, propargylcine, 3-(pyridin-2-yl)-alanine, 3-(pyridin-3-yl)-alanine, 3-(pyridin-4-yl)-alanine, 3-(1-naphthyl)-alanine, 3-(2-naphthyl)-alanine, 2-furylalanine, 3,3-diphenylalanine, 3-benzothienylalanine, 3-thienylalanine, 2-thienylalanine, styrylalanine, 2,3,4,5,6-pentafluorophenylalanine, 1,2,3,4-tetrahydro-isoquininyl-3-carboxylic acid, 1,2,3,4-tetrahydro-β-carbolinyl-3-carboxylic acid, etc.

The term "therapeutically effective amount" refers to an amount of a medicament capable of inhibiting a mammalian disease.

Due to the unique structural features of the compounds of the present invention, they have many therapeutic effects including but not being limited to antibacterial, antiviral, antiinflammatory, antitumor and antidiabetic effects.

2. Studies on Antibacterial Activity of Andrographolide

Andrographis Herb extract has been used for the treatment of acute upper respiratory infection and accompanied nasal sinusitis. The results showed that Andrographis Herb extract exhibited significant effects in comparison with placebo, the patients' symptoms such as headache, malaises of nose and pharyngeal portion and general malaise were significantly alleviated, and the body temperature of patients in the treatment group decreased mildly (Caceres et al., Phytomedicine 1997, 4, 101-104). In a test of 250 subjects, Andrographis Herb extract significantly shortened the course of disease and alleviated symptoms in patients of common cold (Hancke et al., Phytother. Res. 1995, 9, 559-5621; Melchior et al. Phytomedicine 1996, 3, 314-318; Caceres et al., Phytomedicine 1999, 6, 217-223). In a test of 107 eighteen-year students, the subjects were administered with two 100 mg tablets (5.6% Andrographis Herb extract) per day, while this dose was far less than the dose used for clinical treatment of common cold (about 1,200~6,000 mg per day) continuously for three months, and another 53 subjects were administered with placebo. As a result, only 16 subjects in the group of Andrographis Herb got common cold, while 33 subjects in the placebo group got common cold, which proved that Andrographis Herb can reduce risk of the common cold (Caceres et al., Phytomedicine 1997, 4, 101-104).

Although andrographolide has been widely used in clinic, some tests has proven that it has no directly antibacterial effect (Singha et al., Fitoterapia 2003, 74, 692-694; Li et al., China J. Chinese Materia Medica 2006, 12, 1015-1017; Xia et al., J. Immunol. 2004, 173, 4207-4017). Recently, Li et al (China J. Chinese Materia Medica 2006, 12, 1015-1017) found that an andrographolide derivative ("Lianbizhi" or "莲必治") significantly inhibited the QS-system of *Pseudomonas aeruginosa* (PAO1), although it did not directly inhibit the growth of PAO1. At 12.5 mg/mL (34 mM) Lianbizhi did not influence growth of the cultured PAO1, but significantly inhibited the production of *Pseudomonas aeruginosa* and the activities of protease and elastase. This newly discovered mechanism of action may partially explain the antibacterial effects of andrographolide derivatives.

*Staphylococcus aureus* (SA) belongs to Gram-positive bacteria, and usually inhabited in nasal cavity of healthy individuals. Statistic data show that about 1 billion people in the world carry different sub-types of SA (Ryan et al., Sherris Medical Microbiology 2004, 4th ed., McGraw Hill). The infection caused by SA is one of the most common skin infections. The proliferation of SA may cause serious infection and other life-threatening diseases such as endocarditis, pneumonitis, osteomyelitis, septic arthritis, meningitides, postoperative wound infections, septicemia, toxic shock syndrome, etc. (Silverstein et al., Infect. Immun. 1994, 62, 152-

161; Dann et al., Clin. Inf. Dis. 1994, 18, 437-439; Wisplinghoff et al., Pediatr. Infect. Dis. J. 2003, 22, 686-691; Karlowsky et al., Ann. Clin. Microbiol Antimicrob. 2004, 3, 7-15).

With wide application of antibiotics, drug resistance for SA becomes serious. MRSA is one kind of drug-resistance SA, and is resistant to β-lactam antibiotics including methicillin and other commonly used antibiotics such as oxacillin, penicillin and amoxicillin. Recent researches indicated that about 20% patients with infection of SA through intravenous injection were MRSA infection (Graham et al., Ann. Intern. Med. 2006, 144, 318-325).

For those patients with serious infection of drug-resistant SA, vancomycin and teicoplanin may be the only effective treatments. Vancomycin and teicoplanin have poor absorptions with oral administration, so that intravenous injection is necessary for systemic infection. Drug-resistant SA that resists both vancomycin and teicoplanin (VISA) has appeared already (Schito et al., Clin. Microbiol. Infect. 12 Suppl. 2006, 1, 3-8).

*Pseudomonas aeruginosa* (PA) belongs to Gram-negative bacteria and is a conditional pathogenic bacterium. *Pseudomonas aeruginosa* usually infects lung, urethra, burns, etc., and also causes blood infections (Stover et al., Nature 2000, 406, 959-964; Lyczak et al., Microbes. Infect. 2000, 2, 1051-1060). *Pseudomonas aeruginosa* is also the main bacteria causing chronic lung infections in cystic fibrosis patients (Frederiksen et al., Pediatr. Pulmonol. 1997, 23, 330-335), and is recently recognized as one of the main causes of long-term wound infections (Bjarnsholt et al., Anal. Bioanal. Chem. 2007, 387, 409-414).

Bacteria adhere on a surface and form a social colony in a polymer substrate generated by themselves, called biofilm (Costerton et al., Science 1999, 284, 1318-1322). *Pseudomonas aeruginosa* usually forms a biofilm. Under suitable test conditions, *Pseudomonas aeruginosa* may form a biofilm having a thickness of hundreds millimeters, and bacteria living in this biofilm are resistant to antibiotics. In patients with lung infection of *Pseudomonas aeruginosa*, cystic fibrosis patients are particularly suitable for therapies targeting the biofilm.

Many species may achieve a critical density through cell-cell signal transduction, called quorum sensing (QS). Bacterial cells produce and release extracellular autoinducers (autoinducers, AIs) to regulate gene expression and colonial arrangement (formation of biofilm) (Fuqua et al., Curr. Opin. Microbiol. 1998, 1, 183-189; Hammer et al., N. (Engl) J. Med. 1996, 35, 1081-1090). Recently, it is recognized that QS regulating system ensures that symptoms caused by mass proliferation only appear when the bacterial density increases to a level overwhelming the host.

Gram-negative bacteria's acylhomoserine lactone system (AHLs) is the most studied QS system. Although communication among bacteria is a subject matter of microbial ecology, it has been recognized that AHLs is also important in diseases of plants, animals including humans. AHLs were firstly found in the bioluminescence system of *Vibrio fischeri* (Eberhard et al., Biochem. 1981, 20, 2444-2449; Nealson et al., J Bacteriol. 1970, 104, 300-306). *Vibrio fischeri* contains Lux I and Lux R of protein-AI synthetase, and both of them are transcriptional regulatory factors activated by regulating the luminescence operon with AI. AHL molecules produced by AHL synthase contain a homoserine lactone ring (derived from S-adenosyl methionine) and accompany with variable acyl chains (derived from fat metabolism) linked by an amide linkage. AHLs contain 4~18 carbon atoms, which change with oxidation state and unsaturation degree (Fuqua et al., Curr. Opin. Microbiol. 1998, 1, 183-189).

Two colonial sensing pathways mediated by AHL were found in *Pseudomonas aeruginosa*. Las system consists of the AHL synthase gene lasI for synthesizing 3-oxolauroyl-homoserine lactone and the gene lasR for encoding LuxR transcription regulon protein (Gambello et al., J. Bacteriol. 1991, 173, 3000-3009; Zhao et al., Chin. Med. J. (Engl) 1991, 104, 770-775). Some studies show that Las system regulates the expression of causative agents, including exocellular enzymes (LasB elastase, LasA protease, alkaline protease), secondary metabolites (pyocyanin, hydrogen cyanide, pyoverdin), toxins (exotoxin A) and lasI itself. In rhl system, rhlI gene product determines the synthesis of butyryl-homoserine lactone (C$_4$-HSL), and it together with rhlR gene product activate the gene transcription for biosynthesis of rhlAB rhamnolipid. The rhl system also regulates the expression of some causative agents controlled by las system. The structure of 3-oxolauroyl-homoserine lactone is as follows:

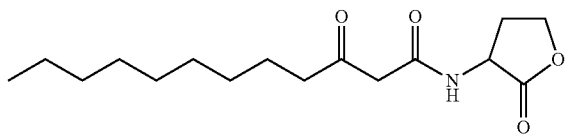 [SMILES: CCCCCCCCCC(=O)CC(=O)NC1CCOC1=O]

The general model of *Pseudomonas aeruginosa* colonial sensing is: when the bacterial colony density is at a lower level, the bacteria produce 3-oxolauroyl-homoserine lactone at a basic level; when the density increases and 3-oxolauroyl-homoserine lactone reaches a critical concentration, it reacts with LasR to form a LasR-3-oxo-C$_{12}$-HSL complex, which can activate the transcription of many genes that express and produce many causative agents such as exocellular enzymes, secondary metabolites and toxins.

During the gene expression regulation of bacterial colony behavior, colonial sensing is a widely-recognized effective mechanism of action. Researches in the last 20 years indicate that the signal pathways of bacterial colony sensing are promising targets for development of novel antibacterial agents.

Andrographolide and its 3 derivatives, potassium dehydroandrograpolide succinate ("Chuanhuning" or "穿琥宁", potassium sodium dehydroandrographolide succinate ("Yanhuning" or "炎琥宁") and andrographolide sodium bisulfite ("Lianbizhi" or "莲比治" can alleviate clinical symptoms of inflammation, fever and bacterial and viral infection diseases (Hendrickson et al., J. Bacteriol. 2001, 183, 7126-7134; Zhang et al., Clin. Exp. Pharmacol. Physiol. 2000, 27, 358-368; Shen et al., Br. J. Pharmacol. 2002, 35, 399-406; Gabrielian et al., Phytomedicine 2002, 9, 589-597). Since they are derived from natural traditional Chinese herb and exhibit good therapeutic effects, they are usually called as "green antibiotics".

Pyretolysis and Anti-Inflammatory Effects of Andrographolide

Andrographolide has pyretolysis and anti-inflammatory effects in fever models induced by 2,4-dinitrophenol or endotoxin, edema models induced by albumen, and inflammation models induced by croton oil. Andrographolide inhibits and delays fever caused by diplococcus pneumoniae and haemolytic beta streptococcus. Andrographolide has pyretolysis effects in rabbits with fever caused by bacterium typhosum or bacterium paratyphosum paratyphoid or in rats with fever caused by 2,4-dinitrophenol, and decrease fever severity in rabbits infected with both diplococcus pneumoniae and haemolytic beta streptococcus cultures. Oral administration of andrographolide in a dose of 30, 100 or 300 mg/kg can significantly inhibit claw edema caused by ocellate chondrus, kaolin and nystatin in rats, and significantly inhibit granuloma caused by cotton balls and relieve edema caused by arthritis. Andrographolide (300 mg/kg) can inhibit the dye leakage caused by acetic acid in a vascular permeability test (Han et al., The Chinese J. Modern Applied Pharmacy 2005, 22, 126-129). Chiou et al (Br. J. Pharmacol. 2000, 129, 1553-1560) reported that andrographolide (1-100 mM) inhibited NO synthesis by reducing the inducible NO synthase (iNOS) expression in RAW264.7 cells, and inhibited de novo protein synthesis and decreased protein stability by accelerating degradation. Batkhuu et al (Biol. Pharm. Bul. 2002, 25, 1169-1174) reported that andrographolide inhibited the production of NO, in a concentration ranging from 0.1~100 mM, and its $IC_{50}$ was 7.9 mM.

Up-regulation of adhesion molecule expression and the increase of endothelium-leucocyte adhesion are important steps for development of inflammatory reaction. Tumor necrosis factor-α (TNF-α) can enhance the endothelium-leucocyte adhesion by increasing expression of endothelial adhesion molecules (ICAM-1). After endothelial cells were cultured for 18 h in the presence of TNF-α (0.5 ng/mL), the adhesion rate increased by 15 times. If andrographolide (0.6-16.7 mg/ml) was added simultaneously, the increase of adhesion caused by TNF-α can be reduced. In the test for the effects of andrographolide on ICAM-1 expression, it was found that andrographolide at 0.6-16.7 mg/mL inhibited the up-regulation of ICAM-1 expression caused by TNF-α in a dose-dependent manner. Shen et at (Br. J. Pharmacol. 2002, 135, 399-406) illustrated that andrographolide inhibited inflammatory reaction through murine neutrophilic granulocyte by regulating PKC-dependent pathway to block or at least partially block the production of reactive oxygen species (ROS) Tsai et al (Euro. J. Pharmacol. 2004, 498, 45-52) evaluated the anti-inflammatory mechanism of andrographolide acting on the macrophages supplementation induced by in vitro complement 5α (C5α). Andrographolide inhibited cell division in a dose-dependent manner, and its $IC_{50}$ was 5.6±0.7 µM. Extracellular signal-regulated kinase 1/2(ERK1/2), P38 mitogen-activated protein kinase (P38MAPK) and phosphatidylinositol-3-kinase (PI3K) were necessary for C5α induced division, whereas c-Jun N-terminal kinase (JNK) was nonessential. Andrographolide significantly attenuated C5a-stimulated phosphorylation of ERK1/2, and of its upstream activator, MAP kinase-ERK kinase (MEK1/2). Under the same conditions, however, andrographolide failed to affect C5a-stimulated p38 MAPK and JNK phosphorylation. Andrographolide also strongly abolished C5a-stimulated Akt phosphorylation, a downstream target protein for PI3K. These results indicate that inhibition of cell division by interfering with ERK1/2 and PI3K/Akt signal pathways may contribute to the anti-inflammatory activity of andrographolide.

Xia et al (J. Immunol. 2004, 173, 4207-4217) reported that andrographolide inhibited nuclear central transcriptional factor (NF-kappaB) activation. Mechanistically, it formed a covalent adduct with reduced cysteine (62) of p50, thus blocking the binding of NF-kappaB oligonucleotide to nuclear proteins. Andro suppressed the activation of NF-kappaB in stimulated endothelial cells, which reduced the expression of cell adhesion molecule E-selectin and prevented E-selectin-mediated leukocyte adhesion under flow. It also abrogated the cytokine- and endotoxin-induced peritoneal deposition of neutrophils, attenuated septic shock, and prevented allergic lung inflammation in vivo. Notably, it had no suppressive effect on IkappaBalpha degradation, p50 and p65 nuclear translocation, or cell growth rates. Hidalgo et al (Br. J. Pharmacol. 2005, 144, 680-686) studied the anti-inflammatory mechanism about andrographolide and reported that andrographolide inhibited the expression of several proinflammatory proteins that exhibit a NF-kappaB binding site in their gene. Hidalgo et al analyzed the effect of andrographolide on the activation of NF-kappaB induced by platelet-activating factor (PAF) and N-formyl-methionyl-leucyl-phenylalanine (fMLP) in HL-60 cells differentiated to neutrophils. It is concluded that andrographolide exerts its anti-inflammatory effects by inhibiting NF-kappaB binding to DNA, and thus reducing the expression of proinflammatory proteins, such as COX-2.

Effects of Andrographolide on Cardiovascular System

Chen et al (Biochem. Pharmacol. 2004, 67, 1337-1345) investigated the molecular mechanisms and signaling pathways by which Andro protects human umbilical vein endothelial cells (HUVECs) from growth factor (GF) deprivation-induced apoptosis. Results demonstrated that HUVECs undergo apoptosis after 18 hr of GF deprivation but that this cell death was suppressed by the addition of Andro in a concentration-dependent manner (1-100 microM). Andro suppresses the mitochondrial pathway of apoptosis by inhibiting release of cytochrome c into the cytoplasm and dissipation of mitochondrial potential (Deltapsi(m)), as a consequence, prevented caspase-3 and -9 activation. Treatment of endothelial cells with Andro induced activation of the protein kinase Akt, an anti-apoptotic signal, and phosphorylation of BAD, a down-stream target of Akt. In conclusion, Andro exerts its anti-apoptotic potential via activation of the Akt-BAD pathway in HUVECs and thus may represent a candidate of therapeutic agent for atherosclerosis.

Hepatoprotective Effects of Andrographolide

The administration of andrographolide in different doses (50, 100, 200, 400 mg/kg) in patients at 48, 24, 2 h before the administration of galactosamine or 1, 4, 7 h after the administration of paracetamol inhibited the increase of concentrations of aspartate aminotransferase (AST) and alanine aminotransferase (ALT), alkaline phosphatase, bilirubin and triacylglycerol induced by galactosamine and paracetamol and restored their normal levels. Andrographolide inhibits rat hepatic injury caused by carbon tetrachloride. Andrographolide (5.0 and 10 mg/kg, p.o.) inhibited activation of liver microsome aniline hydroxylases, N-demethylases and O-demethylases in rats, and was most sensitive to O-demethylases. Visen et al (J. Ethnopharmacol. 1993. 40, 131-136) reported that andrographolide showed a significant dose dependent (0.75-12 mg/kg p.o.) protective activity against paracetamol-induced toxicity on ex vivo preparation of isolated rat hepatocytes. It significantly increased the percent viability of the hepatocytes. It completely antagonized the toxic effects of paracetamol on certain enzymes (GOT, GPT and alkaline phosphatase) in serum as well as in isolated hepatic cells. Andrographolide was found to be more potent than silymarin, a standard hepatoprotective agent.

Hypoglycemic Activity of Andrographolide

Diabetes Mellitus (DM) is a chronic systemic disease relating to genetic factors and many environmental factors, and is a kind of metabolic disorder of sugar, fat and protein caused by absolutely or relatively insufficient secretion of insulin. There are two kinds of diabetes mellitus, insulin-dependent diabetes mellitus (type-I) (IDDM) and non-insulin-dependent diabetes mellitus (type-II) (NIDDM), and more than 80% diabetics are type-II diabetics.

Clinical antidiabetic agents grouped in accordance with their action mechanisms mainly comprise: insulin secretion accelerating agents (such as sulfonylureas: glibenclamide, glipizide, etc.); insulin-sensitizing agents (such as biguanides: phenformin, metformin, etc.); α-glucosidase inhibitors (such as acarbose, miglitol, etc.); and insulin preparations as well as several agents for enhancing metabolism and utilization of glucose. By reviewing hypoglycemic agents used or to be used in clinic, it can be seen that western medicines usually have certain limitations and adverse reactions, even serious adverse reactions, such as hypoglycemia, lactic acidosis, and complications after long term of administration. For example, sulfonylureas have a predominant adverse effect of hypoglycemia; and biguanides may cause lactic acidosis. As for the treatment of type-II diabetes, the oral administration of traditionally sulfonylurease and biguanides usually lead to limit therapeutic effect, and cannot totally prevent further necrosis of beta cells of islet, which may result in insulin dependence. In the recent years, it is found that some traditional Chinese medicines are potent for treatment of diabetes, and besides the above hypoglycemic functions of western medicines; some traditional Chinese medicines further exhibit actions of protecting beta cells of islet, improving hemodynamics, and reducing complications of diabetes (Li Jin and Liu Yaming, Transaction of Shanxi College of Traditional Chinese Medicine, 2006, 7(3):49-51), and thus may achieve a goal of treating the symptoms and causes of diabetes.

During the development of diabetes, there always are complex relationships among high glucose environment, NF-kappaB activation, oxidative stress, inflammation and β-cell apoptosis and diabetic complications.

The high glucose environment of diabetes activates NF-kappaB. Sakiko et al (Am. J. Physiol. Renal. Physiol. 2007, 292, 1141-1150) reported that high glucose condition could promote the expression of kidney glomerulus endotheliocyte ICAM-1 and activate NF-kappaB, while this change could be blocked by some NF-kappaB inhibitors such as pioglitazone. Pieper et al (J. Cardiovasc. Pharmacol. 1997, 30, 528-532) reported that vascular endothelial cells were incubated together with high glucose in different concentrations, the increase of NF-kappaB activity was detected by using electrophoretic mobility shift assay (EMSA), wherein the above effect was blocked by adding an inhibitor SN250 capable of inhibiting NF-kappaB.

Oxidative stress activates NF-kappaB. As for cells present in high glucose environment for a long term, nucleic acids and lipids are in a trend of being oxidized, which results in the formation of non-enzymatic advanced glycosylation end products (AGE), while the latter in turn binds to its receptor (RAGE), affecting cell functions. Mohamed et al (Biofactors, 1999, 10, 157-67) reported that AGE's can lead to increase of intracellular oxidative stress in vitro and in vivo, and then activate NF-kappaB. Consistently, activation of NF-kappaB in diabetics correlates with the quality of glycemic control and can be reduced by treatment with the antioxidant alpha-lipoic acid. Results from mice and human islet cells indicate that activation of NF-kappaB may promote the expression of iNOS and leads to the damage of islet beta cells (Mohamed A. K, et al. Biofactors, 1999, 10, 157-167). Hofmann et al (Diabetologia. 1999, 42, 222-232) observed the activity of NF-kappaB in ex vivo isolated peripheral blood mononuclear cells from 43 patients with type-I diabetes mellitus, in which 10 patients had been treated with antioxidant lipoic acid for two weeks. The results showed that the patients with high level of glycosylated hemoglobin (>10%) showed a significantly increased NF-kappaB activity, and the increase of NF-kappaB activity correlated with the increase of blood plasma lipid peroxidation substances. NF-kappaB activation is at least in part dependent on oxidative stress since lipoic acid reduced NF-kappaB binding activity, and high blood glucose can induce the NF-kappaB activation of blood mononuclear cells in diabetics.

NF-kappaB regulates islet beta cell apoptosis. NF-kappaB regulates the expression of a plurality of genes of proinflammatory factors causing the functional lesions of islet cells. For example, NF-kappaB can promote the killing effects mediated by T cells and the generation of toxicity to beta cells by inducing the expression of Fas and iNOS, COX-2. In addition, the binding sequences of NF-κB exist in promoters of other proinflammatory factors in beta cells, such as chemotactic factors (MCAP-1, etc.) and adhesion molecules (ICAM-1, etc.) (May and Ghosh, Immunol. Today 1998, 19, 80-88). It also had been confirmed in other in vitro models of NF-kappaB inhibition that NF-kappaB plays an important role in the inflammatory reactions of beta cells.

The death of beta cells can be inhibited by inhibiting NF-kappaB activity. Stephens et al (J. Autoimmun. 1997, 10, 293-298) reported that TNF was used to stimulate NIT-1 β-cells of islet, and it was observed that the inhibition of NF-kappaB activity can suppress several different pathways of immune-mediated cell death in beta-cells. Inhibition of NF-kappaB is a potentially effective strategy for protection of pancreatic beta-cells in autoimmune diabetes.

Antioxidants may protect islet beta cells. NO generated by catalysis of induced nitric oxide synthetase (iNOS) is a potential mediator for damage and dysfunction islet of beta cells inflicted by cytokines. Reactive oxidative species (ROS) correlate with the death of beta cells and the development of diabetes. Ho et al (Free Radical Biology Med. 2000, 28, 604-624) reported that ROS scavenger PBN was used to treat alloxan- and STZ-induced diabetes in mice, and the results showed that both alloxan and STZ induced NF-kappaB activation in the pancreas 30 min after their injection, and PBN pretreatment inhibited both alloxan- and STZ-induced activation of NF-kappaB and nitric oxide production, thereby effectively alleviating hyperglycemia.

NF-kappaB Activation and Diabetic Complications

Vascular lesion is a main factor for diabetic complications and mutilation in patients. It has been well recognized that advanced glycosylation end products (AGEs) promote the development of diabetic vascular complications. Schamidt et al (J. Clin. Invest. 1995, 96, 1395-1403) reported that the AGEs isolated from diabetic patients serum induce vascular endothelial cells to express adhesion molecule VCAM-1, in which the induction mechanism relates to NF-kappaB activation, while the oxidative stress caused by AGEs also activate NF-kappaB. Diabetic retinopathy and renal lesions are main causes for blindness and renal lesions nowadays. Romeo et al (Diabetes. 1999, 48 (Sppl), 154) reported that monoclonal antibody immunohistochemisty was employed to compare 13 autopsied diabetic patients to 14 non-diabetic patients with matched age and gender in state of apoptosis of retinal capillary vessel and in occurrence rate of cellular capillaries. The results showed that the group of diabetes had a plurality of NF-κB activated adventitial cells, and showed the increase of apoptosis of endothelial cells and adventitial cells as well as the increase of cellular capillaries, suggesting that the NF-κB activation of retinal adventitial cells of diabetic patients may promote the early damage of diabetic retinopathy. Hofmann et al (Diabetologia. 1999, 42, 222-232) observed 33 diabetic patients, in which 21 patients were complicated by diabetic nephropathy. The results showed that the NF-κB activity of peripheral blood mononuclear cells of patients with diabetic nephropathy increased, the immunohistochemistry staining to the activated NF-κB p65 increased as well, and the NF-kappaB activity was in positive correlation with urinary micro-albumin-extent and plasma thrombomodulin concentration.

In summary, the high glucose environment and oxidative stress in diabetes can activate NF-kappaB. The inflammatory reaction and oxygen radicals of oxidative stress induced by NF-kappaB activation may cause the apoptosis and necrosis of beta-cells, and result in diabetes. In addition, it is also found that diabetic angiopathies, diabetic retinopathies and nephropathies are in positive correlation with NF-kappaB activation. Thus, a novel strategy for treating diabetes may lie in effective NF-kappaB inhibitors and antioxidants to protect beta-cells and prevent the development of diabetic complications.

Andrographolide significantly reduces the blood glucose level in diabetic rats. Zhang and Frei (ASEB J. 2001, 15, 2423-2432) studied the therapeutic effects of an ethanol extract of Andrographis Herb in normal rats and STZ-induced diabetic rats, and reported that oral administration of ethanol extract of Andrographis Herb reduced blood glucose level of diabetic rats in a dose dependent manner. When the oral dose of the extract was 400 mg/kg, its hypoglycemic effect is equivalent to that of metformin (500 mg/kg, oral), but it did not affect the blood glucose level of normal rats.

In a long-term test, after consecutive 14-days oral administration of ethanol extract of Andrographis Herb (400 mg/kg) or metformin (500 mg/kg) twice daily, it was found that the diabetic rats treated with Andrographis Herb or metformin exhibited a significant body weight gain in comparison with the rats of the control group; the rats of the treatment group took less food and water; and no significant effect was found in normal rats. In the Andrographis Herb treatment group, hepatic glucose-6-phosphatase (G-6-Pase) activity decreased significantly, suggesting that the hypoglycemic effect of Andrographis Herb may be related to the increase of glucose metabolism. The study further disclosed that the ethanol extract of Andrographis Herb had not only hypoglycemic effect, but also effects against oxidative stress, and it can increase the contents of superoxide dismutase (SOD), hydrogen peroxidase (CAT) and reduced glutathione (GSH) in liver and kidney tissues of diabetic rats, and reduce lipid peroxidation products (MDA). Oxidative stress is an important factor for diabetic complications, therefore it can be concluded that Andrographis Herb can reduce the occurrence of diabetic complications and the extant of tissue damage. Similarly, Rao (Iranian J. Pharmacol. Ther. 2006, 5, 47-45) also confirmed in an alloxan-induced diabetic rat model that the chloroform extract of Andrographis Herb (300 mg/kg, oral) exhibited hypoglycemic activity and kidney protecting activity, and thus effectively prevented proteinuria and uremia. Yu et al (Planta Med. 2003, 69, 1075-1079) reported that andrographolide (1.5 mg/kg, oral) exhibited significant inhibition on the hyperglycemia of normal rats stimulated by intravenous injection of glucose and the hyperglycemia of STZ-induced diabetic rats.

In vitro soleus muscle glucose uptake test indicated that andrographolide can enhance the uptake of radioactive glucose, and it was further confirmed that this might be related to an enhanced expression of glucose transporter 4 (GLUT4) gene. Glucose transporter is a mediator for the glucose transportation through cell membrane. Researches indicated that the expression of GLUT4 gene in diabetic patients decreased (Sivitz Wi, et al. Nature 1989, 340, 72-74).

Antitumor Effects of Andrographolide

Nanduri et al (U.S. Pat. No. 6,486,196, 2002; Bioorg. Med. Chem. Lett. 2004, 14, 4711-4717) disclosed that 8,17-epoxidized andrographolide maintained the cytotoxicity of lactone, and an esterification derivative improved activity notably. The in vitro test indicated that andrographolides having an $IC_{50}$ of 5-15 μM exhibited activity to various human tumor cells (Satyanarayana et al., BMC Cancer 2003, 4, 26-34). Rajagopa et al (J. Exp. Ther. Oncol. 2003, 3, 147-158) disclosed that andrographolide inhibited the proliferation of many kinds of tumor cell lines. The direct action on tumor cells is to block cycle within $G_0$-$G_1$ phases by inducing cycle inhibitory protein P27 and reducing CDK4 expression. Andrographolide also increases the production of TNF-α and the expression of CD4 marker thereby resulting in the toxicity of lymphocytes to tumor cells, which may be an indirect effect of its anti-tumor activity.

Andrographolide arrests cell cycle within $G_0$-$G_1$ phases, and induces the production of cell cycle inhibitory protein p27 and reduces the expression of cell cycle-dependent protein kinase 4 (CDK4). The effects of andrographolide treatment on cell cycle of MCF-7 cell were analyzed using flow cytometry and western blot (Rajagopal et al., J. Exp. Ther. Oncol. 2003, 3, 147-158). MCF-7 cells were treated with 5 μM andrographolide for 24 and 48 h, and the analysis showed that as compared with the control cells treated with DMSO, after 24 h of andrographolide treatment, the cells of $G_1$ phase increased by 10%, accompanied with a decrease of proportion of cells of S and G2/M phases, which indicated that cell cycle was arrested at $G_1$ phase. After 48 h of treatment, as compared with the control group, the proportion of cells of $G_1$ phase decreased, while the number of cells in S and $G_2$-M phases did not change, but the MCF-7 cells of sub-$G_1$ phase increased by 7%. This indicated that after 24 h of Andrographis Herb treatment, the cells were induced to stay in $G_1$ phase, while if further treatment was performed, the apoptosis of the cells in $G_1$ phase occurred, and an apparent evidence was the increase of sub-$G_1$ phase cells which is a feature of apoptosis.

The results of an in vivo test showed that andrographolide had effects against melanoma (B16F0) and carcinoma (HT-29) in transplantation models (Rajagopal et al., J. Exp. Ther. Oncol. 2003, 3, 147-158). Satyanarayana et al (Satyanarayana et al., BMC Cancer 2003, 4, 26-34) reported that the antitumor activity of andrographolide in mice with MCF-7 breast cancer in hollow fiber system. Andrographolide at a dose of 100 mg/kg inhibited the growth about 50%. The anticancer activity of andrographolide was also proven in HT-29 human colon cancer nude mouse model and B16F0 melanoma mouse model. Andrographolide was orally administered at a dose of 200 mg/kg, twice per day, which inhibited the growth of melanoma and colon cancer by 39% and 52%, respectively.

When andrographolide was used for treatment of rats with MCF-7 human breast cancer, the results of Western blot analysis showed that 100 mg/kg andrographolide significantly enhanced p27 expression in tumors inoculated peritoneally or subcutaneously (Rajagopal et al., J. Exp. Ther. Oncol. 2003, 3, 147-158), while p27 was a main CDK inhibitor for regulating the $G_1$ phase of cell cycle. The level of cell cycle dependent protein kinase, CDK4, decreased only in the tumor-inoculated by peritoneal injection, while did not change in the tumor inoculated by subcutaneous injection. These results showed that andrographolide inhibited the procedure of cell cycle by regulating the expression of cell cycle-associated proteins.

Lipoic Acid

Alpha-lipoic acid (LA) exists in various prokaryotic cells and eukaryotic cells. In human body, lipoic acid is a portion of many 2-oxyacidohydrogenases participating in energy formation, and is a cofactor of some multienzyme complexes (Biewenga et al., Drug Metab. Rev. 1997, 29, 1025-1054). Lipoic acid and its reduced form, dihydrolipoic acid (DHLA), as redox substances, transport electron from dehydrogenase substrate to $NAD^+$. Actually, dihydrolipoic acid has stronger antioxidant activity than lipoic acid. The in vivo and in vitro studies indicated that lipoic acid has many pharmacological and antioxidant functions. Pharmacologically, lipoic acid can improve glucose control, relieve polyneuropathy caused by diabetes, and effectively alleviate heavy metal poisoning. As an antioxidant, lipoic acid directly scavenge free radicals, chelate transition metal ions such as iron and copper ions, increase levels of glutathione and vitamin C in cytoplasm and prevent toxicity caused by their loss. These different functions suggest that lipoic acid may exert its functions through many physiological and pharmacological mechanisms (Smith et al., Curr. Med. Chem. 2004, 11, 1135-1146). Due to the above reasons, lipoic acid is one of the most popular healthy supplements. In Germany, lipoic acid has been approved for the treatment of symptomatic nervous diseases caused by diabetes for more than 20 years. The structure of lipoic acid is as follows:

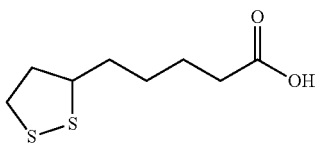 [SMILES: O=C(O)CCCCC1CCSS1]

Lipoic acid is a very strong antioxidant. Lester Packer (Free Radic. Biol. Med. 1995, 19, 227-250) stated that lipoic acid is the strongest bio-antioxidant. This point is derived from many researches. First of all, LA/DHLA can directly scavenge free radicals including hydroxy, hydrogen peroxide, hypochlorous acid and pure oxygen (Packer et al., Free Radic. Biol. Med. 1995, 19, 227-250; Matsugo et al., Biochem. Biophys. Res. Commun. 1996, 227, 216-220). Secondly, they chelate transition metal ions, and have benefit of preventing relative weak oxidants (such as superoxide anions and hydrogen peroxide) from being converted into harmful hydroxy active substances (Matsugo et al., Biochem. Biophys. Res. Commun. 1996, 227, 216-220). Finally, they can regenerate other antioxidants. Antioxidants with redox function maintain their effective function by recirculating from their oxidized forms to their effective reduced forms. DHLA is a strong reducing agent, so that it can recirculate antioxidant in oxidized form (Matsugo et al., Biochem. Biophys. Res. Commun. 1996, 227, 216-220). DHLA can directly regenerate ascorbate and indirectly regenerate vitamin E from their oxidized forms respectively, and can reduce glutathione in oxidized form to its reduced form (Jocelyn, P. C. Eur. J. Biochem. 1967, 2, 327-331). In fact, it was found in either in vitro test or in vivo test that, lipoic acid can increase the content of glutathione in cells (Busse et al., Arzn. Forsch. 1992, 42, 829-831). After lipoic acid was injected to animals, the results showed that glutathione level increased by 30%-70%, especially in lung, liver and kidney cells.

Zhang et al. (FASEB J. 2001, 15, 2423-2432) used human large artery endothelial cells (HAEC) as models, and studied the effects of LA as well as glutathione and vitamin C in the expression of TNF-α induced adhesion molecules and the signal transduction of NF-kappaB. Pretreatment of HAEC with lipoic acid (0.05~1 mmol) for 48 h inhibited NF-kappaB binding activity induced by TNF-α (10 U/ml) in a dose-dependent manner (FIG. 10). When lipoic acid 0.5 mmol/L was used, the NF-kappaB activity induced by TNF-α was inhibited by 81%. The inhibition of lipoic acid on the activation of endothelial cells induced by TNF-α suggested a metal chelation effect, rather than a general antioxidation effect. This explains that the maximum inhibitory effect was achieved after the pretreatment of HAEC with lipoic acid for 48 h, because the chelation of metal ions and the discharge thereof from cells are a slow process.

De Mark et al. (J. Cell Physiol. 2003, 194, 325-340) reported that lipoic acid induced the high acetylation of histone in vivo, and exhibited different effects on the growth and viability of normal cell lines and altered cell lines. Human tumor cell lines FaDu and Jurkat, and Ki-v-Ras-modifed Balb/c-3T3 murine interstitial cell line underwent apoptosis after they were treated with lipoic acid. Correspondingly, after the unmodified cell lines were treated with lipoic acid, their cell cycle was reversibly arrested at $G_0/G_1$ phase. Lipoic acid results in the increase of cell cycle-dependent protein kinase inhibitor level after translation. Animal tests showed that lipoic acid reduced side-effects caused by cyclophosphamide and vincristine, but did not reduce their potencies (Berger et al., Arzneimittelforschung 1983, 33, 1286-1288). Recently, Dovinova, et al (Neoplasma, 1999, 46, 237-241) reported that the combination of lipoic acid (16 mg/kg) and adriamycin (5 mg/kg) increased the survival rate of mice with L1210 leukemia by 67%.

Although the antitumor activity of lipoic acid has been confirmed in vitro, in animal tumor models and in human body, the mechanism of action is still unclear. As aforementioned, lipoic acid can scavenge free radicals, inhibit NF-kappaB activation, increase p27 expression, etc. However, its antitumor activity still cannot be explained by a single mechanism.

Lipoic acid is used for treatment of diabetes and complications. In recent years, some researchers disclosed that the overproduction of superoxide in mitochondrial electron-transport chain is the reason of activating main pathway of hyperglycemia-mediated tissue damage, and that oxidative stress is a common factor for the development of diabetic chronic complications (Brown, L. Nature 2001, 414, 813-820), and the improvement of oxidative stress may be an effective mean for prevention of diabetic chronic complications. Yorek et al (Yorek, M. A. Exp. Diabetes Res., 2004, 5, 123-135) reported that lipoic acid improved the function of vascular endothelium of diabetic patients. Clinical researches suggest that antioxidants can improve the symptoms of autonomic nerves of diabetic patients (Ziegler D, et al., Diabetologia, 1995, 38, 1425-1433). Oral administration of α-lipoic acid in a short term can increase the peripheral insulin sensitivity of type II diabetic patients, thereby reducing blood glucose level and cardiovascular complications (Kamenova P. Hormones (Athens), 2006, 5, 251-258).

In summary, the natural product, andrographolide has been used for a very long time, and is safe. In particular, the abovementioned researches indicate that it exerts many effects such as antitumor, immuno-regulation, antiinfection, antiinflammation, liver protection and hypoglycemic effects.

3. Therapeutical Methods and Dosage Forms

Oral compositions can be prepared according to any known methods in the art for the preparation of a pharmaceutical composition, and may comprise one or more compounds selected from sweetening compounds, flavoring compounds, coloring compounds and preservative compounds, in order to provide a pharmaceutically palatable preparation. Tablets comprise an active compound admixed with pharmaceutically acceptable nontoxic excipients suitable for production of tablets. These excipients can be inert diluents, such as calcium carbonate or alginic acid, or adhesive compounds such as starch, gelatin or Arabic gum, and lubricant compounds such as magnesium stearate, stearic acid or talc powder. Tablets may or may not have a coating, or may be coated according to known methods to delay the disintegration and absorption in gastrointestinal tract, thereby providing a long-term sustained effect. For example, glyceryl stearate may be used to prolong the action period of medicine.

Oral dosage forms may also be hard capsules in which an active ingredient is mixed with inert solid diluent such as calcium carbonate, calcium phosphate or kaolin, or may be soft capsules in which an active ingredient is mixed with aqueous or oily medium such as peanut oil, liquid paraffin or olive oil.

Aqueous suspensions comprise an active ingredient admixed with excipients suitable for the production of aqueous suspensions, in which the excipients can be suspending compounds, such as carboxymethylcellulose sodium, sodium alginate, polyvinylpyrrolidone, tragacanth gum and Arabic gum, dispersing or wetting compounds such as natural phospholipids such as lecithin or products of condensation polymerization of fatty acid and alkene oxides such as heptadecanyl ethoxylated cetyl alcohol or products of condensation polymerization partially derived from fatty acids and ethoxylated hexitol such as polyoxyethylene-sorbitol oleate, or products of condensation polymerization partially derived from fatty acid and ethoxylated hexitol such as polyoxyethylene-sorbitan oleate. Aqueous suspensions further comprise one or more preservatives, such as vinyl parahydroxybenzoate or n-propyl parahydroxybenzoate, as well as one or more coloring compounds, one or more flavoring compounds, one or more sweetening compounds such as sucrose or saccharin.

Oily suspensions can be prepared by suspending an active ingredient in plant oils or mineral oils, in which the plant oils include peanut oil, olive oil, sesame oil or coconut oil, and the mineral oils include paraffin oil. Oily suspensions can comprise thickening compounds such as beeswax, hard paraffin, or acetyl alcohol. Sweetening compounds as aforementioned and flavoring compounds can be added to provide dosage forms suitable for oral administration. Antioxidants such as ascorbic acid can be added to these compositions for preservation.

Dispersible powders and granules suitable for preparing aqueous suspensions by adding water comprise an active ingredient admixed with dispersing or wetting compounds, suspending compounds and one or more preservatives. Suitable dispersing or wetting compounds and suspending compounds are those exemplified above. Additional excipients such as sweetening compounds, flavoring compounds and coloring compounds may also be added.

The pharmaceutic compositions of the present invention can also be O/W emulsions, in which oil phase can be plant oil such as olive oil and peanut oil or mineral oil such as liquid paraffin or a mixture thereof Suitable emulsifying agents can be natural gums such as Arabic gum, tragacanth gum, natural phospholipids such as soybean phospholipids, lecithin, esters or partial esters derived from fatty acids and hexitol, acid anhydrides such as anhydro-sorbitol, and products of condensation polymerization of the aforementioned partial esters and ethylene oxides. Additional sweetening compounds, flavoring compounds and coloring compounds may also be added.

Syrups can be prepared by using glycerol, propionic acid-glycerol-sorbitol or sucrose. Syrups can further comprise demulcents, preservatives, flavoring compounds and coloring compounds. Pharmaceutical compounds can be injectable sterile aqueous or oily suspension. This suspension can be prepared by using those suitable dispersing or wetting compounds known in the art and aforementioned suspending compounds. Sterile injectable preparations can further be injectable sterile solutions or suspensions in nontoxic physiologically acceptable diluents or solvents, such as solution of 1,3-butanediol. These acceptable excipients further comprise solvents, such as water, Ringer solution, and isotonic chloride solution. In addition, sterile oil mixtures usually may be used as solvents or suspending media. For this purpose, any moderate mixture oils comprising synthetic monomers or diglycerides can be used, and fatty acid such as oleic acid can be used in injectable dosage forms.

Active compound can also be administered in suppositories suitable for rectal administration. Such compositions can be prepared by mixing the active compound with suitable nonirritant excipients, which can be solid at room temperature but become liquid at rectal temperature and melt in rectum to release the active compound. Such excipients include cocoa butter and polyethylene glycol and the like.

Active compound can be in a sterile medium as excipient for parenteral administration, and can be either suspended or dissolved in the excipient depending on the particular excipients and the concentration of the compound. Additional adjuvants such as topical anesthetics, preservatives and buffering compounds can be dissolved in the excipient.

The compositions of the present invention can be administered continuously or discontinuously by any routes which are compatible with particular molecules. Suitable administration routes can be oral or parenteral administration, including subcutaneous, intravenous, inhale, nasal and intraabdominal administration. In addition, discontinuous administration can be performed by periodically injecting bolus once per day, once per two days, once per three days, once per week, twice per week, once per two weeks, twice per month, and once per month.

The therapeutic compound of the present invention can be provided with individual directly (such as by injection, embedding, or topical administration at tissue sites) or systemically (parenterally or orally) in any suitable manner, in which the compound can be in a composition for parenteral administration, such as intravenous, subcutaneous, ophthalmic, peritoneal, intramuscular, buccal, rectal, vaginal, subepidermal, cutaneous, tracheal, intracerebral, intracranial, intraspinal, intraventricular, intrathecal, intracisternal, intracapsular, intranasal administration or via aerosol. Preferred compositions comprise a portion of water or physiologically compatible liquid suspension or solution. Thus, the vehicles or excipients are physiologically acceptable so that they can carry the composition needed by patients but do not affect the electrolyte and volume balances of patients. Therefore, liquid medium can comprise conventional physiological saline or buffer solution with a pH of 3~7.4. That is, the therapeutic composition of the present invention can also be used continuously or pulsatily administered via a mini pump.

Beneficial solutions for parenteral administration can be prepared according to any methods in the art, such as those described in REMINGTON'S PHARMACEUTICAL SCIENCES (Gennaro, A., ed.), Mack Pub., 1990. The dosage forms of the therapeutical agents according to the present invention can comprise, for example, polyalkylidene glycol such as polyethylene glycol, plant oil, hydrogenated naphthalene. In particular, the dosage forms for direct administration can comprise glycerol and other hyperviscous compositions for maintaining the dosage forms at desired sites. Biocompatible, preferably bioabsorbable polymers comprising hyaluronic acid, collagen, tricalcium phosphate, polybutyrate, cyclic diester and glycolide polymers, as well as cyclic diester/glycolide copolymers are beneficial excipients for in vivo release control of agents. Other potentially beneficial parenteral delivery systems for these agents include ethylene-vinyl acetate copolymer particles, osmotic pump, implantable infusions and liposomes. Dosage forms for inhale administration comprise excipients such as lactose or aqueous solution such as polyoxyethylene(9)lauryl ether, cholylglycine and deoxycholate, or oil solutions for nasal drip, or gels for intranasal application. Parenteral dosage forms can further comprise glycocholate for oral administration, methoxysalicylate for rectal administration, or cutric acid for vaginal administration. Rectal suppositories can further be prepared by mixing the therapeutical compound and nonirritant excipients (alone or combination with chemotherapy agents), in which the excipients can be cocoa butter or other compositions that are solid at room temperature but become liquid at body temperature.

The novel compound of the present invention can also be administered as an injection obtained by dissolving, suspending or emulsifying it in water or nonaqueous solvents. Methylsulfoxide, N,N-dimethylacetamide, N,N-dimethylformamide, plant oils or analog oils, synthetic fatty acids, glycerides, esters of higher fatty acids, and propylene glycol are examples of the nonaqueous solvents. The compound is preferably formulated in aqueous solution, such as Hank's solution, Ringer's solution or physiological saline buffer solution.

The andrographolide derivative according to the present invention can be processed as a dosage form for oral administration, by combining it with pharmaceutically acceptable vehicles known in the art, and the vehicles allow the compound to form tablets, suspensions, liquids or gels for oral administration. The oral dosage form can be prepared by various methods, comprising mixing solid excipients with the compound, optionally grinding the obtained mixture, adding suitable processing granular aids. The follows are some examples of excipients for oral dosage form: sugars such as lactose, sucrose, mannose and sorbitol; starches such as corn starch, wheat starch, potato starch, gelatin, astragalus gum; celluloses such as methylcellulose, hydroxypropylmethylcellulose, hydroxymethylcellulose sodium and polyvinylpyrrolidone (PVP).

The andrographolide derivative according to the present invention can further be aerosols for spraying release from pressurized plug, spraying apparatus or dry-powder inhaler. In spraying apparatus, a suitable propellant comprises dichlorodifluoromethane, trichlorofluoromethane, dichlorotetrafluoroethane, and carbon dioxide. In an example of pressurized spraying apparatus, the dose of the compound can be controlled by regulating a valve.

Dosage forms for topical administration on skin can be prepared by dispersing the compound of the present invention in a dermatologically acceptable vehicle such as lotion, cream, ointment or soap. Particularly beneficial vehicles can form a film or layer on skin for topical administration and suppressing migration. In dosage forms for topical administration on internal tissue surface, agents can be dispersed in liquid or other known substrate so that it can be adhered on the tissue surface to enhance adsorption. The dosage forms can further comprise pectin for coating tissue surface.

The compound of the present invention can be used as an anticancer agent for treatment of cancers or drug-resistant tumors, or as an antimicrobial agent for treatment of bacterial and viral infections. The novel andrographolide derivatives of the present invention are also suitable for use as antidiabetic drugs. They can be administered alone or in combination with other therapeutic agents.

The pharmaceutical composition of the present invention comprises a therapeutically effective amount of andrographolide derivative. An appropriate dose of the compound of the present invention can be determined according to patients' body weight, severity of disease, administration route and physician's judgment. The therapeutically effective amount of andrographolide derivative can be determined by those skilled in the art with their ordinary skills.

Although the therapeutically effective amount of andrographolide derivative varies according to patients to be treated, an appropriate amount of the compound typically is about 1 mg/kg to about 1 g/kg.

In some cases, doses exceeding the specified range are needed, and these are explicit for physicians. Necessarily, physicians will know when and how to suspend, regulate or terminate therapy according to the response of particular patients.

The present invention is further illustrated by referring to the following examples, but these examples are not intended to further restrict the present invention. Obviously, those skilled in the art could modify the materials and methods without departing from the purpose and spirit of the present invention. The efficiency of the compound of the present invention can be detected in vivo and animal models according to the following measurements.

4. Examples

The following examples are provided for description of the present invention in detail, but are not for restricting the scope of the present invention.

Example 1

Preparation of 3,19-isopropylidene-andrographolide 1

Andrographolide (150 mg, 0.43 mmol) was dissolved in a mixture solution of 2,2-dimethoxypropane (0.2 mL), pyridinium p-toluene-sulfonate (3 mg) and toluene/DMSO (3 mL/0.4 mL), stirred at 80° C. for 1 hour, and cooled to room temperature at the end. The reaction was terminated by using triethylamine (0.1 mL), the reaction mixture was diluted with toluene (20 mL), washed with water (3×5 mL), the organic layer was dried using anhydrous $Na_2SO_4$ and concentrated, and the obtained white solid was washed with ethyl ether and filtrated to obtain the compound 1 (130 mg, 78%) (Srinivas et al., Bioorg. Med. Chem. Lett. 2004, 14, 4711-4717).

Example 2

Preparation of 14-lipoyl-3,19-isopropylidene-andrographolide 2

Ethyl chloroformate (0.11 mL) was added to a solution of α-lipoic acid (214 mg) in $CH_2Cl_2$ (8 mL), then triethylamine 0.21 mL was added, and the resultant mixture was stirred under nitrogen gas atmosphere at 0° C. for 1 h. The compound 1 (100 mg) was dissolved in $CH_2Cl_2$ (8 mL), added to the mixture, and stirred at room temperature for 2 days. After the end of reaction, the reaction mixture was diluted with $CH_2Cl_2$ (30 mL), washed in order with aqueous solution of $NaHCO_3$ and water. The organic layer was dried with anhydrous $NaSO_4$, and concentrated under vacuum. The obtained mixture was separated by using a silica gel column to obtain the compound 2 as a yellow crystal powder (90 mg, 61%). $^1H$ NMR ($CDCl_3$, 400 MHz): δ 7.03 (t, 1H, J=5.20 Hz), 5.90 (d, 1H, J=6.50 Hz), 4.90 (s, 1H), 4.20 (dd, 1H, J=7.20, 17.20 Hz), 3.90 (d, 1H, J=11.99 Hz), 1.42 (s, 3H), 1.37 (s, 3H), 1.21 (s, 3H), 0.81 (s, 3H). MS (EST) $[M+H]^+$ m/z 578.

Example 3

Preparation of 14-lipoyl-3,19-dihydroxy-andrographolide AL-1

The compound 2 (100 mg) was added to an acidic aqueous solution (AcOH/H$_2$O=7/3, 3 mL), and stirred at room temperature for 1 h. The reaction mixture was added to water and NaHCO$_3$, and extracted with CH$_2$Cl$_2$ (3×20 mL). The organic layer was dried with anhydrous NaSO$_4$, and concentrated under vacuum. The resultant mixture was separated by using a silica gel column to obtain the compound AL-1 as a yellow crystal powder (42 mg, 45%). $^1$H NMR (CDCl$_3$, 400 MHz): 7.03 (t, 1H, J=5.20 Hz), 5.93 (d, 1H, J=6.50 Hz), 4.88 (s, H), 4.50 (s, 1H), 4.24-4.17 (dd, 1H, J=6.80, 18.40 Hz), 3.34-3.32 (d, 1H, J=10.79 Hz), 1.34 (s, 6H). HRMS [M]$^+$ m/z 538.2417, (calcd 538.2408).

The reaction scheme is as follows:

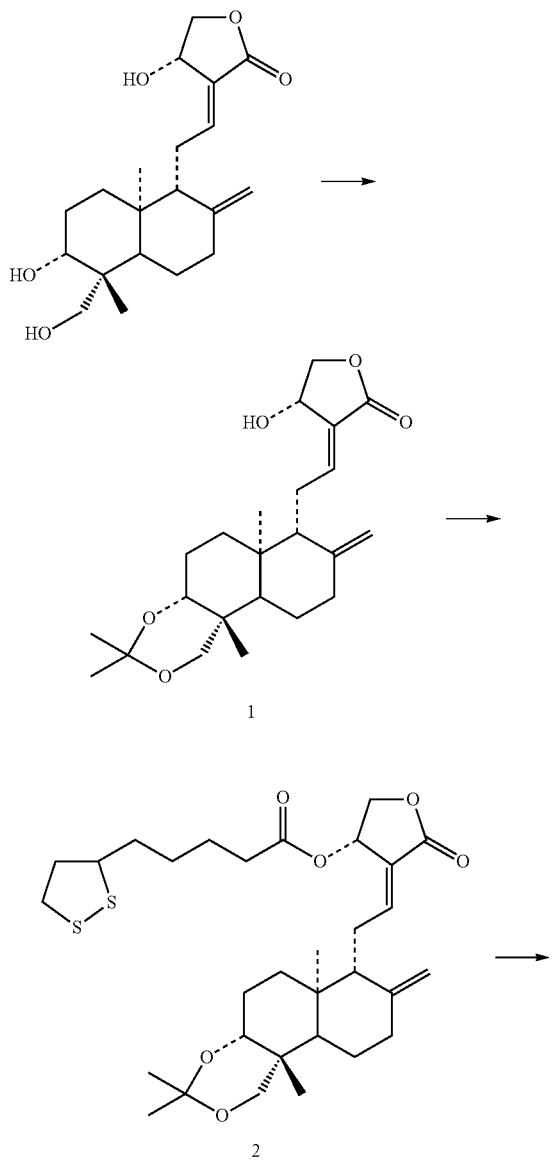

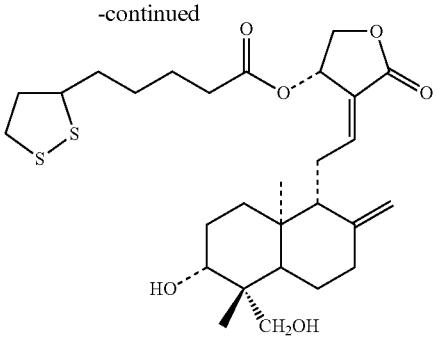

AL-1

Example 4

Preparation of 14-[4'-fluorocinnamyl]-3,19-isopropylidene-andrographolide 3

Ethyl chloroformate (56 μL) was added to a solution of 4'-fluorocinnamic acid (85 mg) in CH$_2$Cl$_2$ (4 mL), then triethylamine (107 μL) was added, and the mixture was stirred under nitrogen gas atmosphere at 0° C. for 1 h. The compound 1 (100 mg) was dissolved in CH$_2$Cl$_2$ (4 mL), added to the mixture, and stirred at room temperature for 2 days. After the end of reaction, the reaction mixture was diluted with CH$_2$Cl$_2$ (40 mL), washed in order with aqueous solution of NaHCO$_3$ and water. The organic layer was dried with anhydrous NaSO$_4$, and concentrated under vacuum. The obtained mixture was separated by using a silica gel column to obtain the compound 3 (85 mg).

Example 5

Preparation of 14-[4'-fluorocinnamyl]-3,19-dihydroxy-andrographolide AF

The compound 3 (70 mg) was added to an acidic aqueous solution (AcOH/H$_2$O=7/3, 2 mL), stirred at room temperature for 1 h. The reaction mixture was added to an aqueous solution of NaHCO$_3$, and extracted with CH$_2$Cl$_2$ (3×20 mL). The organic layer was dried with anhydrous NaSO$_4$, concentrated under vacuum. The resultant mixture was separated by using a silica gel column to obtain the compound AF (45 mg).

Example 6

Preparation of 14-[4'-chlorocinnamyl]-3,19-isopropylidene-andrographolide 4

Ethyl chloroformate (56 μL) was added to a solution of 4'-chlorocinnamic acid (95 mg) in CH$_2$Cl$_2$ (4 mL), then triethylamine (107 μL) was added to the resultant mixture, and stirred under nitrogen gas atmosphere at 0° C. for 1 h. The compound 1 (100 mg) was dissolved in CH$_2$Cl$_2$ (4 mL), added to the mixture, and stirred at room temperature for 2 days. After the end of reaction, the reaction mixture was diluted with CH$_2$Cl$_2$ (40 mL), washed in order with an aqueous solution of NaHCO$_3$ and water. The organic layer was dried with anhydrous NaSO$_4$, and concentrated under vacuum. The obtained mixture was separated by using a silica gel column to obtain the compound 4 (68 mg).

Example 7

Preparation of 14-[4'-chlorocinnamyl]-3,19-dihydroxy-andrographolide ACl

The compound 4 (45 mg) was added to an acidic aqueous solution (AcOH/H$_2$O=7/3, 2 mL), and stirred at room temperature for 1 h. The reaction mixture was added to water and NaHCO$_3$, and extracted with CH$_2$Cl$_2$ (3×20 mL), and the organic layer was dried with anhydrous NaSO$_4$, concentrated under vacuum. The obtained mixture was separated by using a silica gel column to obtain the compound ACl (40 mg).

Example 8

Preparation of 14-[4'-nitrocinnamyl]-3,19-isopropylidene andrographolide 5

Ethyl chloroformate (56 μL) was added to a solution of 4'-nitrocinnamic acid (100 mg) in CH$_2$Cl$_2$ (4 mL), then triethylamine (107 μL) was added, and the resultant mixture was stirred under nitrogen gas atmosphere at 0° C. for 1 h. The compound 1 (100 mg) was dissolved in CH$_2$Cl$_2$ (4 mL), added to the mixture, and stirred at room temperature for 2 days. After the end of reaction, the reaction mixture was diluted with CH$_2$Cl$_2$ (40 mL), and washed in turn with NaHCO$_3$ aqueous solution and water. The organic layer was dried with anhydrous NaSO$_4$, and concentrated under vacuum. The obtained mixture was separated by using a silica gel column to obtain the compound 5 (115 mg).

Example 9

Preparation of 14-[4'-nitrocinnamyl]-3,19-dihydroxy-andrographolide ANO

The compound 5 (95 mg) was added to an acidic aqueous solution (AcOH/H$_2$O=7/3, 3 mL), and stirred at room temperature for 1 h. The reaction mixture was added to water and NaHCO$_3$, and extracted with CH$_2$Cl$_2$ (3×20 mL). The organic layer was dried with anhydrous NaSO$_4$, concentrated under vacuum. The obtained mixture was separated by using a silica gel to obtain the compound ANO (60 mg).

The reaction scheme for synthesis of the compounds AF, ACl and ANO is as follows:

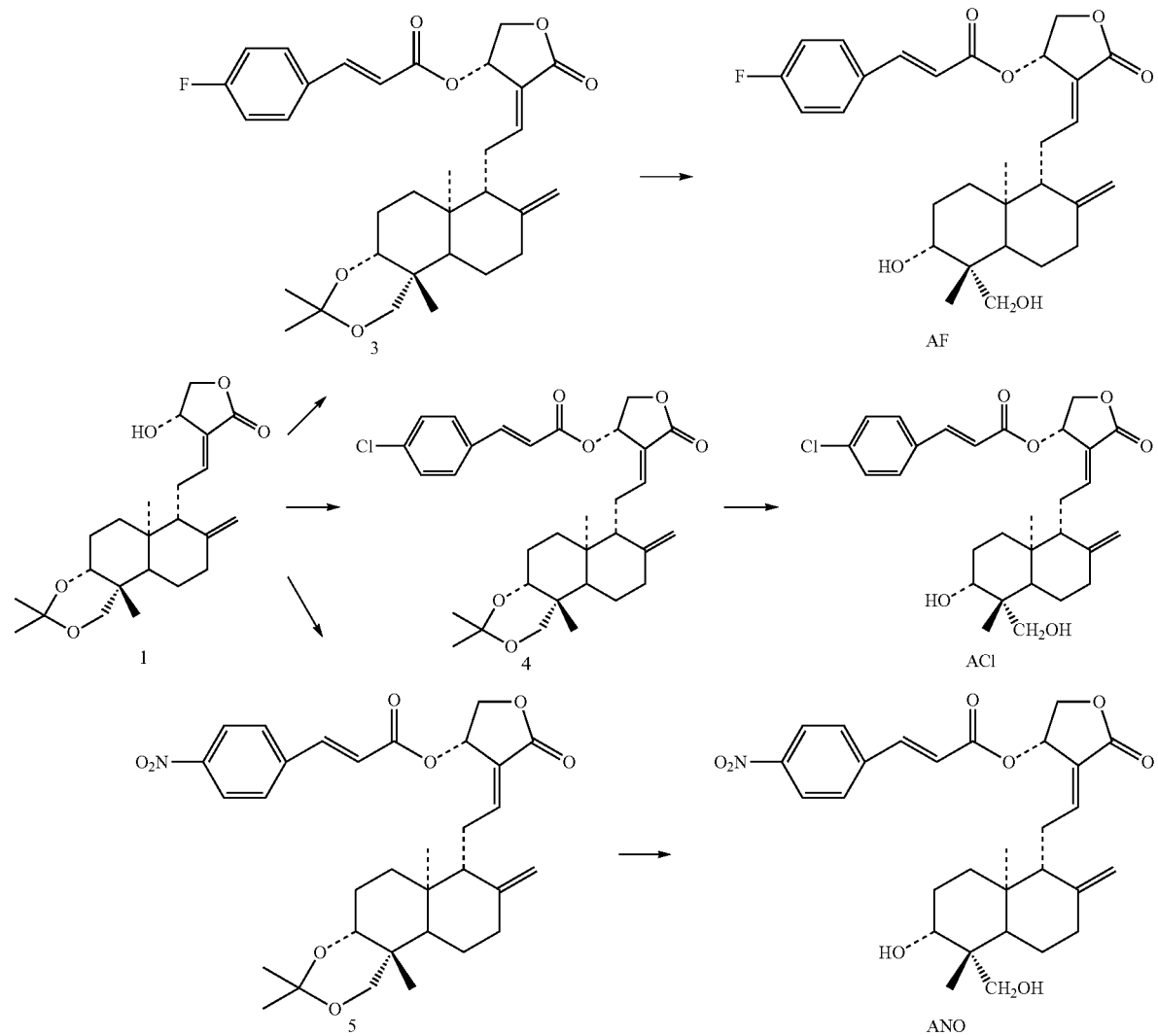

Example 10

In Vitro Antitumor Activity to L1210 Leukemia Cells

L1210 cells ($1.5$-$2.0 \times 10^5$ cells/mL) were separately inoculated in 96-well plate (90 μL/well), andrographolide derivative with a series of gradient diluted concentrations and the positive control medicine doxorubicin hydrochloride (Dox, 10 μL/well). The cells were cultured in an incubator at 37° C., 5% $CO_2$ and saturated humidity for 48 h. Then 5 mg/mL MTT (20 μL/well) was added and cultured at the same conditions for 4 h, DMSO (150 μL/well) was added, and the (570/630 nm) absorbance (A values) was measured by using microplate reader.

Table 1 shows the in vitro antitumor activity to L1210 leukemia cells. The data in Table 1 indicate that the novel andrographolide derivatives exhibit more potent antitumor activity than andrographolide as well as Chuanhuning, Yanhuning and Lianbizhi.

TABLE 1

| Compound | $IC_{50}$ (μM) |
| --- | --- |
| Andro | $28.74 \pm 6.19$ |
| AL-1 | $8.04 \pm 1.92$ |
| ANO | $9.96 \pm 2.25$ |
| Chuanhuning | >100 |
| Yanhuning | >100 |
| Lianbizhi | >100 |

Example 11

Detection of Cell Cycle and Apoptosis

L1210 cells ($1.5$-$2.0 \times 10^5$ cells/mL) were separately inoculated in 6-well plates (4 mL/well), andrographolide derivatives were added. The cells were cultured in an incubator at 37° C., 5% $CO_2$ and saturated humidity. The culture medium was removed, the cells were washed with PBS twice, fixed at −20° C. overnight. Then the cells were centrifuged again, washed with PBS to remove ethanol, cultured with RNase A (200 μg/mL, Sigma) at 37° C. for 1 h, stained with PI (50 μg/mL, Sigma) in dark for 30 min, and detected by using a flow cytometer.

Andrographolide derivatives AL-1 and ANO with a concentration of 10 μM were able to arrest L1210 cells at $G_1$ prophase after 12 h, i.e., induce apoptosis; while andrographolide arrested L1210 cells at $G_0$-$G_1$ phase; the positive control Dox arrested L1210 cells at $G_2$ phase; and the clinically used andrographolide derivatives, Chuanhuning, Yanhuning and Lianbizhi did not change the cell cycle of L1210 cells (see FIGS. 1~8). Andrographolide derivative AL-1 exhibited a cytotoxicity not only 3-times greater than that of andrographolide, but also inducing the apoptosis of L1210 cells.

Example 12

Inhibition Zone Test

Holing method (Chitnis et al., Mol. Microbiology 1993, 8, 583-589) was employed, and Andro, AL-1, ANO, Chuanhuning, Yanhuning and Yanbizhi were separately added to flat plates of LB solid medium comprising *staphylococcus aureus* and drug resistance strains thereof (MRAS5676 and 5677), *E. Coli, Bacillus subtilis, Pseudomonas aeruginosa*, and to flat plats containing YP solid medium comprising *albicans monilia*. After being cultured at 37° C. for 24 h, the sizes of inhibition zones were measured. Table 2 show in vitro antimicrobial activity. As shown in Table 2, Andro and the three clinically used andrographolide derivatives, Yanhuning, Chuanhuning and Lianbizhi did not exhibit any antibacterial activity, while the newly synthesized andrographolide derivatives, AL-1 and ANO, not only inhibited wild type *staphylococcus aureus*, but also exhibited antibacterial activity to meticillin-resistance strain MRSA5676 and 5677.

TABLE 2

| | Inhibition zone diameter (mm) | | | | | | |
| --- | --- | --- | --- | --- | --- | --- | --- |
| | | *Pseudomonas* | *Bacillus* | *Staphylococcus aureus* | | | *Candida* |
| Compound | *E. coli* | *aeruginosa* | *Subtilis* | Wild type | MRSA 5676 | MRSA 5677 | *albicans* |
| Andro [a] | b | b | b | b | b | b | b |
| AL-1 [a] | b | b | b | $4.9 \pm 0.81$ | $6.9 \pm 0.80$ | $4.1 \pm 0.77$ | b |
| ANO [a] | b | b | b | $8.3 \pm 0.99$ | $8.1 \pm 0.64$ | $6.4 \pm 0.42$ | b |
| Chuanhuning [a] | b | b | b | b | b | b | b |
| Yanhuning [a] | b | b | b | b | b | b | b |
| Lianbizhi [a] | b | b | b | b | b | b | b |
| Positive Control | Gentamicin $20.1 \pm 1.00$ | Gentamicin $21.0 \pm 1.00$ | Streptomycin $22.1 \pm 1.00$ | Streptomycin $21.2 \pm 1.00$ | Vancomycin $20.0 \pm 1.00$ | Vancomycin $21.0 \pm 1.00$ | Nysfungin $10.00 \pm 1.00$ |

Streptomycin 0.15 mg/well, gentamicin 0.10 mg/well, vancomycin 0.15 mg/well, nysfungin 0.10 mg/well;
[a] represents standard deviation of the repeated three tests, compounds 0.05 mg/well;
[b] incompetence (inhibition zone diameter <4 mm).

Example 13

Test of Minimal Inhibitory Concentration (MIC)

By using two-fold dilution, Andro, AL-1 and ANO, Chuanhuning, Yanhuning and Lianbizhi were separately added to a 96-well plate containing LB liquid culture medium comprising *staphylococcus aureus* and drug resistance strain thereof (MRAS5676 and 5677), and cultured at 37° C. for 24 h, and absorbance (595 nm) values were measured.

Table 3 shows the MICs of compounds for *staphylococcus aureus* and drug resistance strains thereof; As shown in Table 3, the newly synthesized andrographolide derivatives, AL-1 and ANO exhibited good antibacterial activity, while Andro, Chuanhuning, Yanhuning and Lianbizhi gave MIC of >1 mM.

TABLE 3

| Strain | Andro | AL-1 | ANO | Chuanhuning | Yanhuning | Lianbizhi | Vancomycin |
|---|---|---|---|---|---|---|---|
| Wild type | c | 1000 | 62.5 | c | c | c | 1.56 |
| MRSA5676 | c | 1000 | 62.5 | c | c | c | 1.56 |
| MRSA5677 | c | 1000 | 25 | c | c | c | 3.13 | c no activity (>1 mM).

Example 14

Measurement of Growth Curve of *Pseudomonas aeruginosa*

*Pseudomonas aeruginosa* was inoculated in LB medium, and cultured at a constant temperature of 37° C. in a shaker overnight. The control group is LB medium, and drug groups are LB medium comprising Andro, AL-1, ANO, Chuanhuning, Yanhuning or Lianbizhi. The *Pseudomonas aeruginosa* liquid which had been cultured for 12 h was added to the media of the control and drug groups separately so that the initial $A_{600}$ was 0.05, and co-cultured at 37° C., the absorbance values (A values) of bacterial liquids at wavelength of 600 nm were measured at different time.

As shown in FIG. 2, when the concentration of medicine was 1 mM, AL-1 significantly inhibited the growth of bacteria, Andro exhibited weak antibacterial activity, while the clinically used Chuanhuning, Yanhuning and Lianbizhi had no direct inhibition effect on the growth of *Pseudomonas aeruginosa*.

Example 15

Measurement of Pyocyanin

*Pseudomonas aeruginosa* was inoculated in LB medium, then cultured at a constant temperature of 37° C. in a shaker overnight. The control group was PB medium, and drug groups were PB media comprising Andro, AL-1, ANO, Chuanhuning, Yanhuning or Lianbizhi. The culture media of *Pseudomonas aeruginosa* which had been cultured for 12 h was added to the media of the control and test groups separately so that the initial $A_{600}$ was 0.05, and after being cultured for 3-4 h, the $A_{600}$ values were 0.3-0.5, the culture media of *Pseudomonas aeruginosa* were added to the media of the control and drug groups separately, so that the bacterial solutions to be tested had an initial $A_{600}$ of 0.05, then the bacterial liquids were cultured simultaneously at 37° C. for 18 h, and centrifuged. The supernatant was taken and extracted in turn with chloroform and 0.2 N HCl, and $A_{520}$ values were measured (Zielinshi et al., Biol. Chem. 1991, 266, 9754-9763; May et al., Clin. Microbiology Rev. 1991, 4, 191-206).

The test results of secretion of pyocyanin showed that all compounds were able to inhibit the secretion of pyocyanin (see FIG. 3). These compounds have an order of pyocyanin-inhibition activity as follows: AL-1>Andro>ANO. AL-1 has the highest activity. It should be noted that the concentrations of AL-1 and ANO in the test were only 1/10 of those of Chuanhuning, Yanhuning and Lianbizhi.

Example 16

Measurement of Extracellular Protease

*Pseudomonas aeruginosa* was inoculated in LB liquid, and cultured at a constant temperature of 37° C. in a shaker overnight. The control group was PTSB medium, and the drug groups were PTSB media comprising Andro, AL-1, ANO, Chuanhuning, Yanhuning or Lianbizhi. The culture medium of *Pseudomonas aeruginosa* which had been cultured for 12 h was added to the media of the control and test groups separately, so that the initial $A_{600}$ values of the bacterial liquid to be tested were 0.05, the culture medium of *Pseudomonas aeruginosa* was added to the media of the control and drug groups, so that the initial $A_{600}$ values of the bacterial solutions to be tested were 0.05. After the bacterial liquids were cultured simultaneously at 37° C. for 6 h and centrifuged, supernatant 100 µL was taken, azo-casein 5 mg was added, 1 mM Tris (pH 7.2) 10 mM and $CaCl_2$ 10 mM were added, and then they were shaken for reaction at 37° C. for 6 h, and the reaction was terminated by adding EDTA-Na. The $A_{440}$ values of the supernatants were measured (Zielinshi et al., Biol. Chem. 1991, 266, 9754-9763; May et al., Clin. Microbiology Rev. 1991, 4, 191-206).

Figures 1, 2, 3, 4, 5:
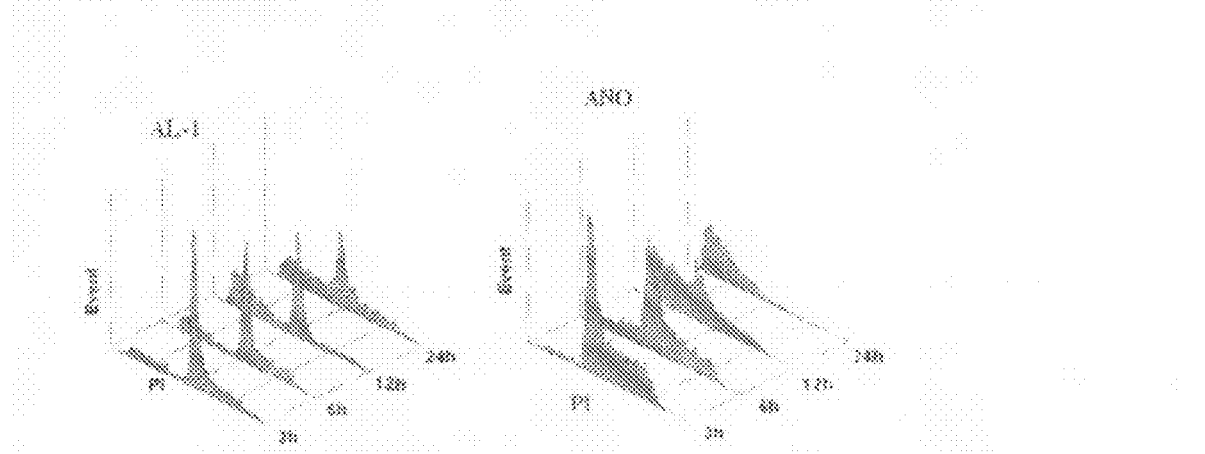
Figures 1, 2, 3, 4, 5, 6, 7, 8:
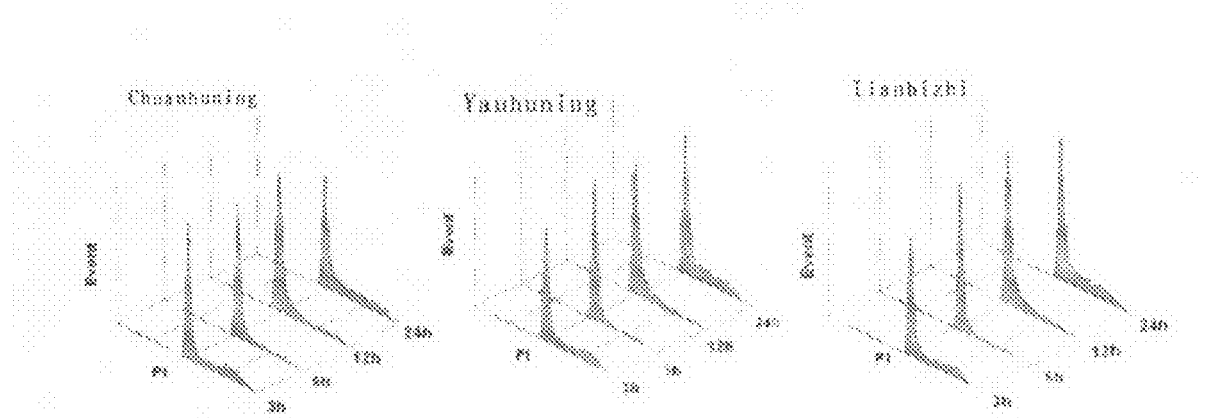
Figure 2:
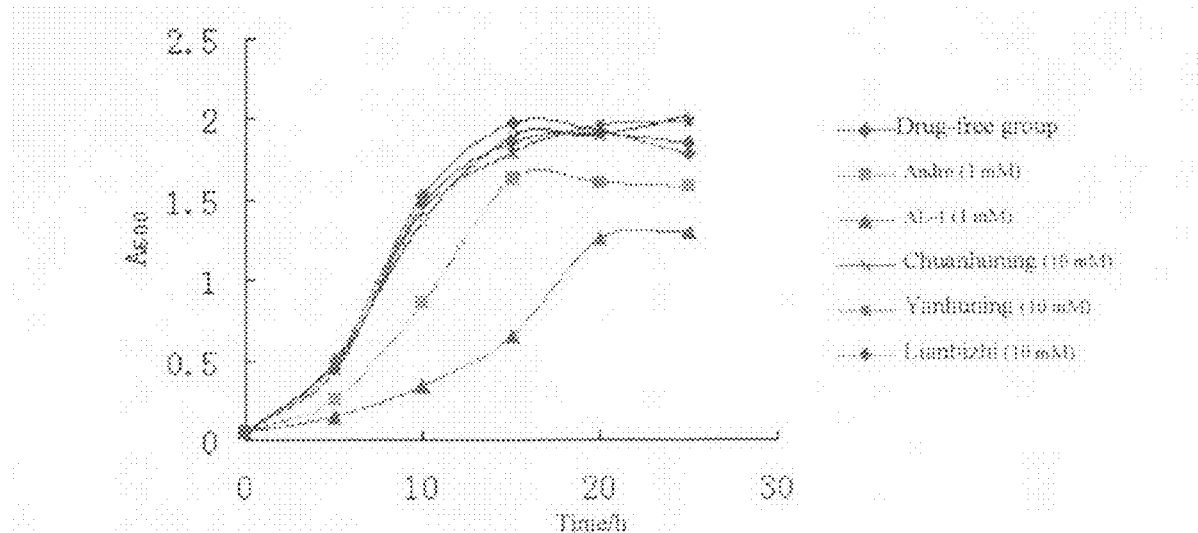
Figure 3:
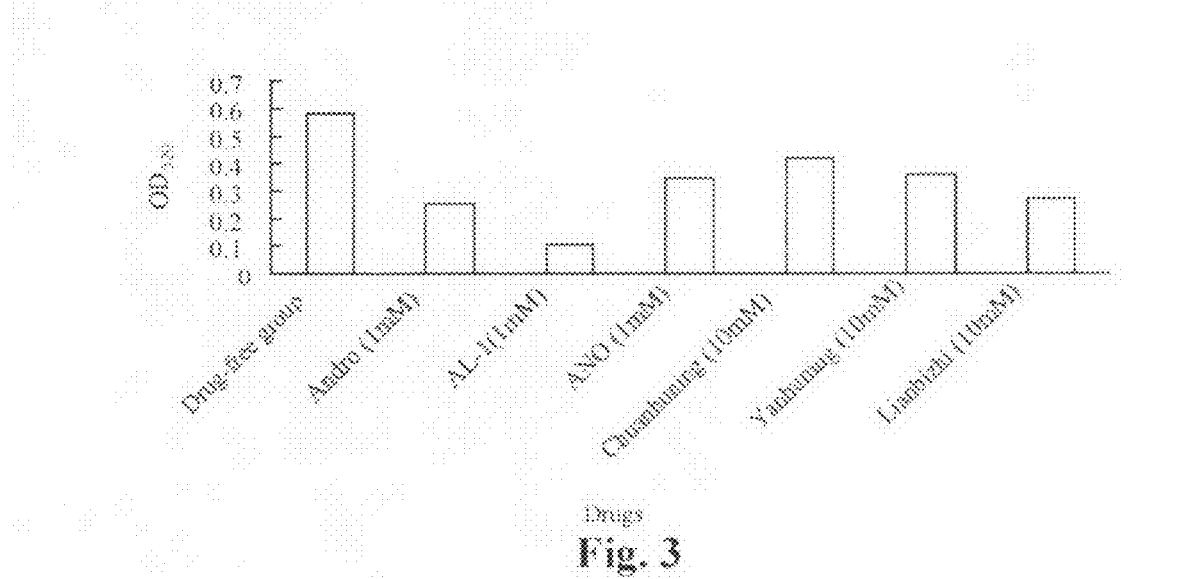
Figure 4:
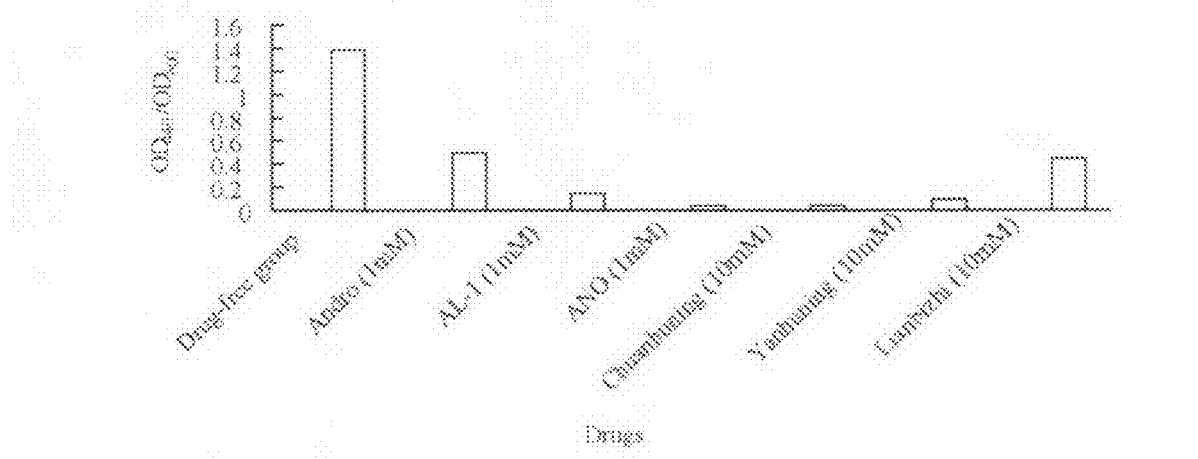
Figures 1, 6:
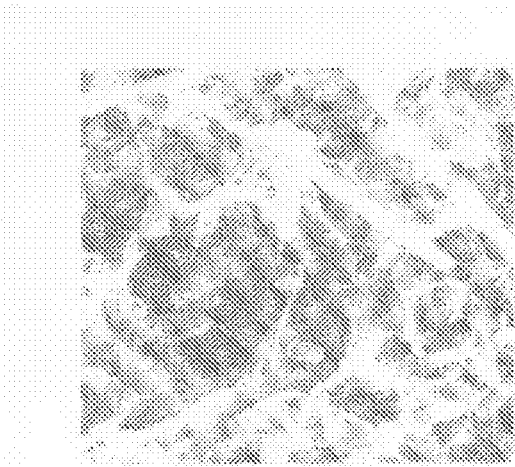
Figures 2, 6:
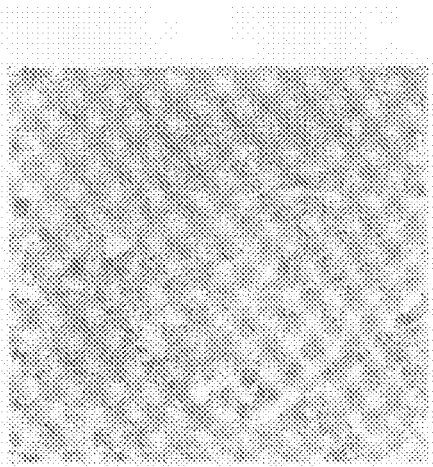
Figures 3, 6:
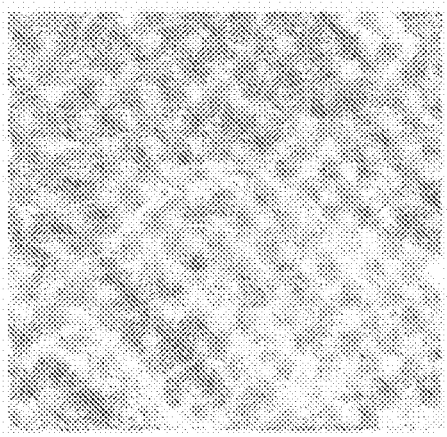
Figures 4, 6:
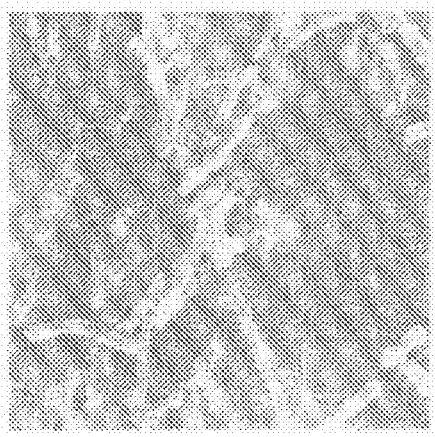
Figures 1, 7:
Figures 2, 7:
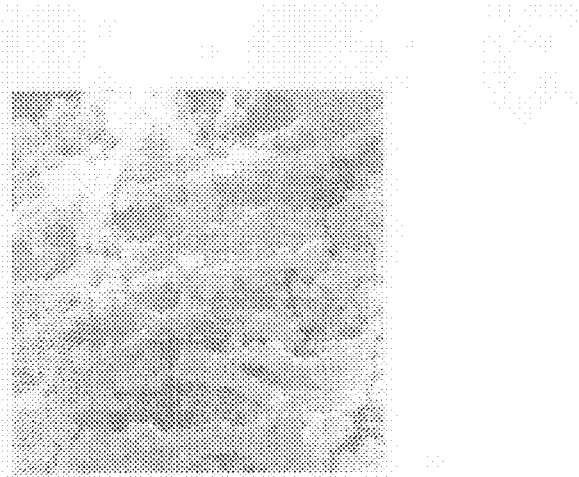
Figures 3, 7:
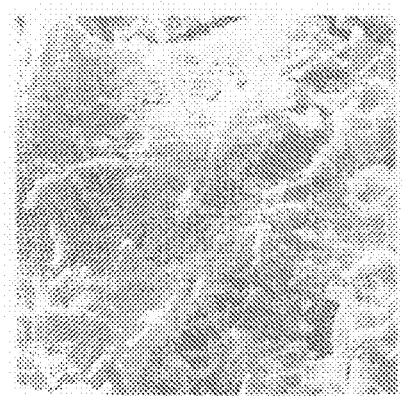
Figures 4, 7:
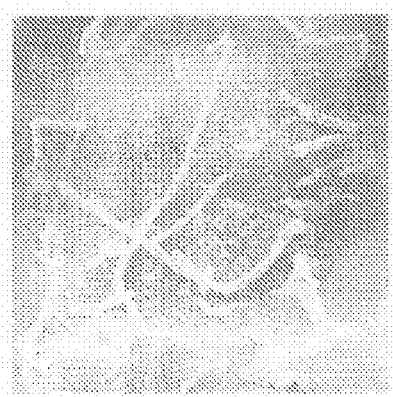

All compounds were able to inhibit the production of extracellular protease (see FIG. 4). These compounds have an order of inhibition activity to extracellular protease as follows: AL-1>ANO>Andro. It should be noted that the concentrations of Andro and ANO in the test were only 1/10 of those of Chuanhuning, Yanhuning and Lianbizhi.

Example 17

Atomic Force Microscope (AFM) Experiment

*Pseudomonas aeruginosa* was inoculated in LB liquid, shaken and cultured at a constant temperature of 37° C. overnight, and the bacterial liquid was centrifuged, washed with sterile physiological saline twice, and mixed with physiological saline to form a bacterial suspension having a turbidity of 0.5 McFarland Standard (bacterial number was about $5 \times 10^{8-9}$ CFU/mL). The bacterial suspension was diluted with physiological saline 50-times. The control group was MHB medium, the drug groups were MHB media comprising Andro or AL-1. After contacting with medicines for 15 h, 1 mL culture solution was added in a sterile centrifuge tube and centrifuged at 10,000×g for 5 min. The supernatant liquid was discarded, and the obtained bacterial sample was washed with double distilled water twice, and suspended in double distilled water. A small volume of *Pseudomonas aeruginosa* suspension was taken and dropped on a cover slip carefully. After water was dried under atmospheric condition, the bacteria were observed by CP-Research type atom force microscope (U.S.A., Thermomicroscopes Co.) (Paster et al., Antimicro. Chemother. 1994, 34, 679-685; Wicken et al., Antimicro. Agents Chemother. 2000, 44, 682-687; Nickel et al., Urology 1986, 135, 586-588).

It can be seen from FIG. 5 that the growth of *Pseudomonas aeruginosa* in the drug groups was significantly inferior to that in the control group, while the bacteriostasis for novel compound AL-1 was significantly superior to that for Andro. *Pseudomonas aeruginosa* treated with AL-1 (1 mM) did not form a confertim bacterial colony, which visualized that the QS system of *Pseudomonas aeruginosa* was directly destroyed by AL-1.

Example 18

Scanning Electron Microscopy (SEM) Experiment

*Pseudomonas aeruginosa* was inoculated in LB liquid, and cultured at a constant temperature of 37° C. in a shaker overnight, and the bacterial liquid was centrifuged, washed with sterile physiological saline twice, and mixed with physiological saline to form a bacterial suspension having a turbidity of 0.5 McFarland Standard (bacterial number was about $5 \times 10^{8-9}$ CFU/mL). The bacterial suspension was diluted with physiological saline 50-times. A biofilm (BF) carrier was placed in a tube containing 2 mL of the bacterial liquid, and the culturing was conducted at 37° C. On the $3^{rd}$ day, an early BF was formed on the surface of the carrier; and on the $7^{th}$ day, a mature BF was formed (Walters et al., J. Antimicro. Chemother. 2003, 47, 317-323). Medium was replaced every other two days. The formation of BF was observed by using Quanta 400 thermal field emission scanning electron microscope (FEI Company). The carrier adhered with BF was washed with sterile physiological saline to remove floating bacteria, fixed with 2.5% glutaral, immersed in pH 7.4 PBS for three times, dewatered in turn with 50%, 70%, 80% and 90% ethanol once, then dewatered with 100% ethanol twice and with tert-butanol twice, 5 min for each time, and lyophilized for 5 h. The surface of carrier was plated with gold under vacuum. The formation of BF was confirmed by SEM observation.

The observation results of BF under SEM showed that the early BF (see FIG. 6) or mature BF (see FIG. 7) after being treated with AL-1 was less than that in the control group, which indicated that AL-1 was able to destroy the BF of *Pseudomonas aeruginosa*. Andro did not significantly inhibit the formation of BF; while the clinically used Chuanhuning, even at a high concentration of up to 10 mM (other compounds were 1 mM), did not destroy the BF of *Pseudomonas aeruginosa*; which indicated that Andro had weak ability to destroy the BF of *Pseudomonas aeruginosa*. This further confirmed the strong potency of AL-1 to destroy the formation of BF of *Pseudomonas aeruginosa*.

Example 19

Experiment of Combination with Antibiotics

In clinic, Erythromycin and Ciprofloxacin are relatively effective medicines for treatment of *Pseudomonas aeruginosa* infections. As aforementioned, natural Andro in combination with erythromycin or ciprofloxacin exhibits synergistic effects. Thus, an antibacterial experiment of a combination of AL-1 with erythromycin or ciprofloxacin was performed by using suspended *Pseudomonas aeruginosa*. The application of ciprofloxacin alone led to a survival rate of 85%, while the combination of ciprofloxacind and AL-1 led to a survival rate of 54.9% (see Table 4, which shows the survival rates of *Pseudomonas aeruginosa* treated with different medicines). The erythromycin led to a survival rate of 93.9%, while the combination of erythromycin and AL-1 gave a survival rate of 40.8%. The combination of ciprofloxacin and erythromycin resulted in a survival rate of 35.7%. It can be seen that the combination of erythromycin and AL-1 showed almost equivalent effects as the combination of ciprofloxacin and erythromycin. It is more important that the combination of AL-1 with ciprofloxacin and combination of AL-1 with erythromycin exhibited bacteriostasis far greater than the combination of Andro with ciprofloxacin and the combination of Andro with erythromycin. This further proves that AL-1 has better therapeutical effects than Andro.

TABLE 4

| Medicine | Survival Rate (%) |
|---|---|
| Ciprofloxacin (0.017 μg/mL) | 85 |
| Erythromycin (3.75 μg/mL) | 93.9 |
| Andro (350 μg/mL) | 90.1 |
| AL-1 (538 μg/mL) | 84 |
| Ciprofloxacin (0.017 μg/mL) + erythromycin (3.75 μg/mL) | 35.7 |
| Ciprofloxacin (0.017 μg/mL) + Andro (350 μg/mL) | 65.3 |
| Ciprofloxacin (0.017 μg/mL) + AL-1 (538 μg/mL/mL) | 54.9 |
| Erythromycin (3.75 μg/mL) + Andro (350 μg/mL) | 63.5 |
| Erythromycin (3.75 μg/mL) + AL-1 (538 μg/mL/mL) | 40.8 |

The molar concentration of Andro (350 μg/mL) and AL-1 (538 μg/mL) was the same, that was 1 μmol/mL. The treated *Pseudomonas aeruginosa* was cultured for 15 h, and A values were measured by $OD_{600}$.

Example 20

Therapeutical Effects on STZ-Induced Diabetes Mellitus in Rats

30 Female SD rats, 180-220 g, fasted for 16 h, were subjected to intraperitoneal injection of 60 mg/kg of STZ (purchased from Sigma Company). After 72 h, blood samples were collected from the rats by cutting their tails after fasting 16 h, and blood glucose values were measured by using a blood glucose analyzer (Johnson & Johnson Company). The diabetic rats were divided into 4 groups: Vehicle control group, Andro (100 mg/kg) group, AL-1 (160 mg/kg) group and glibenclamide (0.6 mg/kg) positive control group, 4 rats per group, and other 4 normal rats were used as normal control group. Animals were weighed, orbital bleeded, and the sera were separated. According to the instructions of kit (Zhejiang Dongou Biotechnology Co., Ltd.), the contents of triglyceride and total cholesterol were measured. The animals of the test groups were treated with Andro, AL-1 or glibenclamide separately by intragastric administration, once per day, for consecutive 7 days. The rats of vehicle group were treated with an equivalent volume of solvent (20% DMSO in $H_2O$). After being fasted for 16 h, the rats were weighed, and bleeded for the measurement of blood glucose, triglyceride and total cholesterol. The obtained data were processed by using one-factor analysis of variance (One-way ANOVA) followed by Student's t-test. Table 5 shows the therapeutic effects of AL-1 on STZ-induced diabetes mellitus in rats. As shown in Table 5, after the diabetic rats were treated for one week, Andro and AL-1 protected the rats from the loss of weight, and this effect was equivalent to that of glibenclamide. As for hypoglycemic effect, AL-1 was significantly superior to Andro (equivalent concentration), and was equivalent to the positive control glibenclamide, i.e., AL-1 reduced blood glucose level by about 66%. In addition, AL-1 and Andro also decreased triglyceride and total cholesterol levels in diabetic rats.

TABLE 5

| Index | Day | Solvent control | Andro | AL-1 | Glibenclamide |
|---|---|---|---|---|---|
| Body weight (g) | 0 | 196.33 ± 11.93 | 198.33 ± 10.69 | 214.33 ± 9.81 | 201 ± 3.61 |
|  | 7 | 170 ± 3.05 | 194 ± 5.66 [a] | 191.67 ± 7.64 [b] | 195 ± 1.41 [a] |
| Blood glucose (mmol/L) | 0 | 24.93 ± 4.97 | 22.15 ± 0.35 | 19.53 ± 1.90 | 26.9 ± 1.56 |
|  | 7 | 23.6 ± 3.06 | 18.6 ± 0.28 | 6.63 ± 2.41 [b, c] | 9.25 ± 0.64 [b, c] |
| Total triglyceride (mmol/L) | 0 | 7.36 ± 1.03 | 8.44 ± 2.45 | 6.28 ± 0.78 | 7.84 ± 2.21 |
|  | 7 | 6.78 ± 0.96 | 2.04 ± 0.38 [b, c] | 4.79 ± 0.45 [c] | 1.9 ± 0.8 [b, c] |
| Total cholesterol (mmol/L) | 0 | 2.87 ± 1.4 | 3.15 ± 1.67 | 3.39 ± 0.59 | 2.57 ± 1.09 |
|  | 7 | 2.15 ± 0.05 | 1.61 ± 0.26 [a] | 1.95 ± 0.63 [a] | 1.86 ± 0.29 [c] |

The changes of body weight, blood glucose level, total triglyceride and total cholesterol in the rats with STZ-induced diabetes mellitus before and after 7 days of the treatment with AL-1: the $0^{th}$ day represents the values before the treatment, and the $7^{th}$ day represents the values after consecutive 7 days of treatment. Each group has 4 rats, and the obtained data were denoted as average ± standard deviration,

[a] $P < 0.05$,

[b] $P < 0.01$ in comparison with the solvent control.

[c] $P < 0.05$ in comparison with the $0^{th}$ day (One-way ANOVA followed by Student's t-test).

What is claimed is:

1. An andrographolide derivative, having a structure of the formula I:

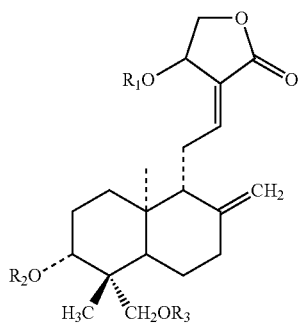

wherein $R_1$, $R_2$ and $R_3$ are the same or different groups selected from hydrogen, substituted or unsubstituted organic acid radicals, inorganic acid radicals, alkyl, aryl or heteroaryl, and at least one of $R_1$, $R_2$ and $R_3$ is R-lipoic acid, S-lipoic acid or a racemic lipoic acid, or its corresponding dihydrolipoic acid, or a N-acetylcysteine radical.

2. The andrographolide derivative according to claim 1, further having a structure of the formula II:

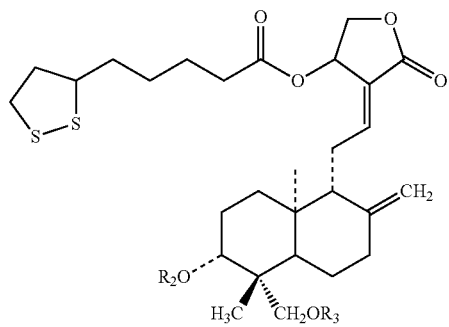

wherein the organic acid radicals are fatty acid radicals or aromatic acid radicals, the fatty acid radicals are selected from acetic acid radical, propionic acid radical, butanoic acid radical, malonic acid radical, pyruvic acid radical, cinnamic acid radical, succinic acid radical, citric acid radical, lactic acid radical, gluconic acid radical, lipoic acid radical, N-acetylcysteine or amino acid radical; the aromatic acid radicals are benzoic acid radical; the inorganic acid radicals are sulfuric acid radical, nitric acid radical or phosphoric acid radical.

3. The andrographolide derivative according to claim 2, further having a structure of the formula AL-1:

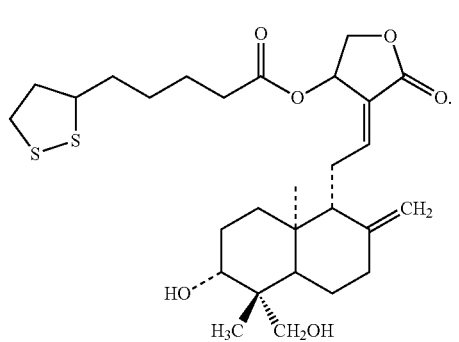

4. The andrographolide derivative according to claim 1, further having a structure of the formula III:

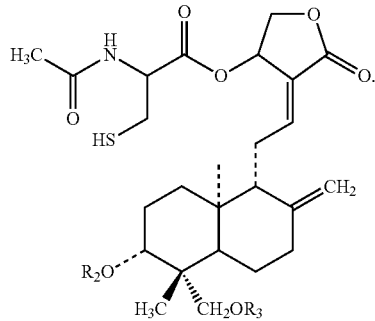

5. The andrographolide derivative according to claim 4, further having a structure of the formula A-AC:

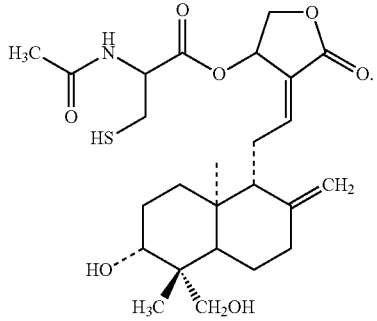

A-AC

6. An andrographolide derivative, having a structure of one of the following formulas:

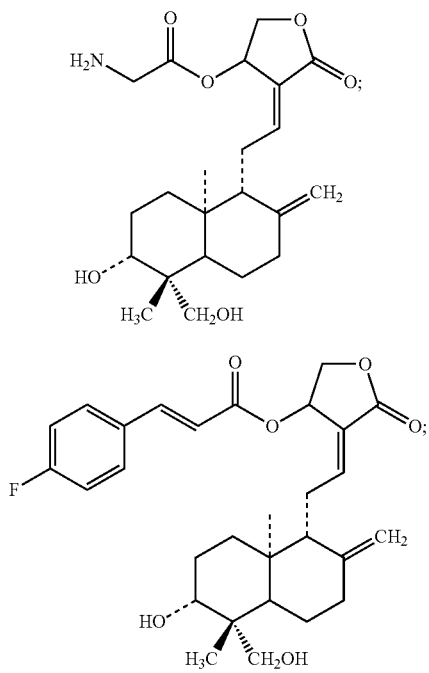

AG

AF

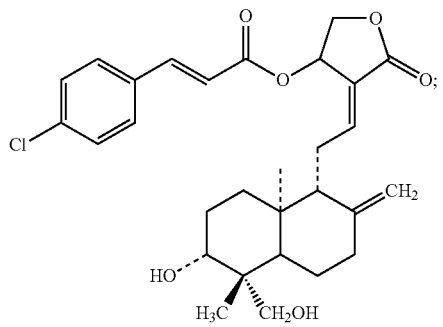

ACl

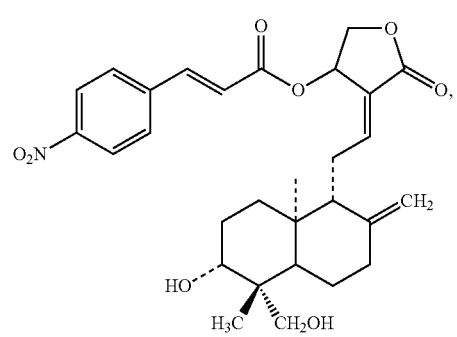

ANO or pharmaceutically acceptable salts thereof.

7. A method for treatment of leukemia, comprising administering to a patient in need of the treatment an andrographolide derivative according to claim 1 or a composition thereof.

8. A pharmaceutical composition comprising a combination of an andrographolide derivative according to claim 1 and an antibiotic agent.

9. The pharmaceutical composition according to claim 8, wherein the antibiotic agent is ciprofloxacin.

10. A method of manufacturing a medicament comprising:
   providing the andrographolide derivative according to claim 1 or a composition thereof; and
   combining the andrographolide derivative or composition with a carrier.

11. The method of claim 10, wherein the andrographolide derivative is present in an amount sufficient for treatment of leukemia.

\* \* \* \* \*

UNITED STATES PATENT AND TRADEMARK OFFICE
CERTIFICATE OF CORRECTION

PATENT NO.       : 8,367,720 B2                                            Page 1 of 1
APPLICATION NO.  : 12/672476
DATED            : February 5, 2013
INVENTOR(S)      : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 380 days.

Signed and Sealed this

First Day of September, 2015

Michelle K. Lee
*Director of the United States Patent and Trademark Office*